(12) United States Patent
Ishida

(10) Patent No.: US 11,684,756 B2
(45) Date of Patent: Jun. 27, 2023

(54) CATHETER ASSEMBLY

(71) Applicant: TERUMO KABUSHIKI KAISHA, Tokyo (JP)

(72) Inventor: Masahiro Ishida, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 383 days.

(21) Appl. No.: 16/280,899

(22) Filed: Feb. 20, 2019

(65) Prior Publication Data
US 2019/0175878 A1 Jun. 13, 2019

Related U.S. Application Data

(63) Continuation of application No. PCT/JP2017/029719, filed on Aug. 21, 2017.

(30) Foreign Application Priority Data

Aug. 25, 2016 (JP) ................... 2016-164497

(51) Int. Cl.
*A61M 25/06* (2006.01)
*A61M 25/00* (2006.01)

(52) U.S. Cl.
CPC .... *A61M 25/0606* (2013.01); *A61M 25/0097* (2013.01); *A61M 25/0618* (2013.01); *A61M 2025/0006* (2013.01)

(58) Field of Classification Search
CPC .......... A61M 25/0606; A61M 25/0612; A61M 25/0097; A61M 25/0631;
(Continued)

(56) References Cited

U.S. PATENT DOCUMENTS 4,828,549 A * 5/1989 Kvalo ............... A61M 25/0606
604/164.07
5,690,619 A 11/1997 Erskine
(Continued)

FOREIGN PATENT DOCUMENTS

JP 2009-504242 A 2/2009
JP 2013-529111 A 7/2013
(Continued)

OTHER PUBLICATIONS

International Searching Authority, "International Search Report," issued in connection with International Patent Application No. PCT/JP2017/029719, dated Nov. 7, 2017.
(Continued)

*Primary Examiner* — Kami A Bosworth
*Assistant Examiner* — Antarius S Daniel
(74) *Attorney, Agent, or Firm* — Foley & Lardner LLP

(57) ABSTRACT

A catheter assembly includes a first assembly including a catheter and a catheter hub, a second assembly including an inner needle and a housing, and a catheter operating member. The catheter assembly also includes a separation restricting mechanism separate from the housing. The separation restricting mechanism restricts separation of the first assembly and the catheter operating member in an inserted state in which the inner needle is inserted in the catheter, and allows the separation of the first assembly and the catheter operating member in a non-inserted state in which the inner needle is separated from the catheter.

6 Claims, 30 Drawing Sheets

(58) Field of Classification Search
CPC .......... A61M 2025/0006; A61M 25/01; A61M 25/0113; A61M 25/0637

See application file for complete search history.

(56) References Cited

U.S. PATENT DOCUMENTS

| | | | |
|---|---|---|---|
| 8,932,258 B2* | 1/2015 | Blanchard | |
| 2004/0044313 A1* | 3/2004 | Nakajima | A61M 25/0637 604/533 |
| 2015/0231364 A1* | 8/2015 | Blanchard | A61M 25/0618 604/164.08 |

FOREIGN PATENT DOCUMENTS

| | | |
|---|---|---|
| JP | 2014-517729 A | 7/2014 |
| JP | 2017-176455 A | 10/2017 |
| WO | WO-2011/118643 A1 | 9/2011 |
| WO | WO-2013/171851 A1 | 11/2013 |
| WO | WO-2014/199697 A1 | 12/2014 |

OTHER PUBLICATIONS

International Searching Authority, "Written Opinion," issued in connection with International Patent Application No. PCT/JP2017/029719, dated Nov. 7, 2017.

Translation of the Written Opinion of the International Searching Authority dated Nov. 7, 2017 in corresponding application No. PCT/JP2017/029719.

Office Action dated Jul. 20, 2021 in counterpart Japanese Patent Application No. 2018-535651, (9 pages).

Notice for Reasons of Refusal in Japanese Patent Appl. No. 2018-535651, dated Mar. 22, 2022 (14 pages).

* cited by examiner

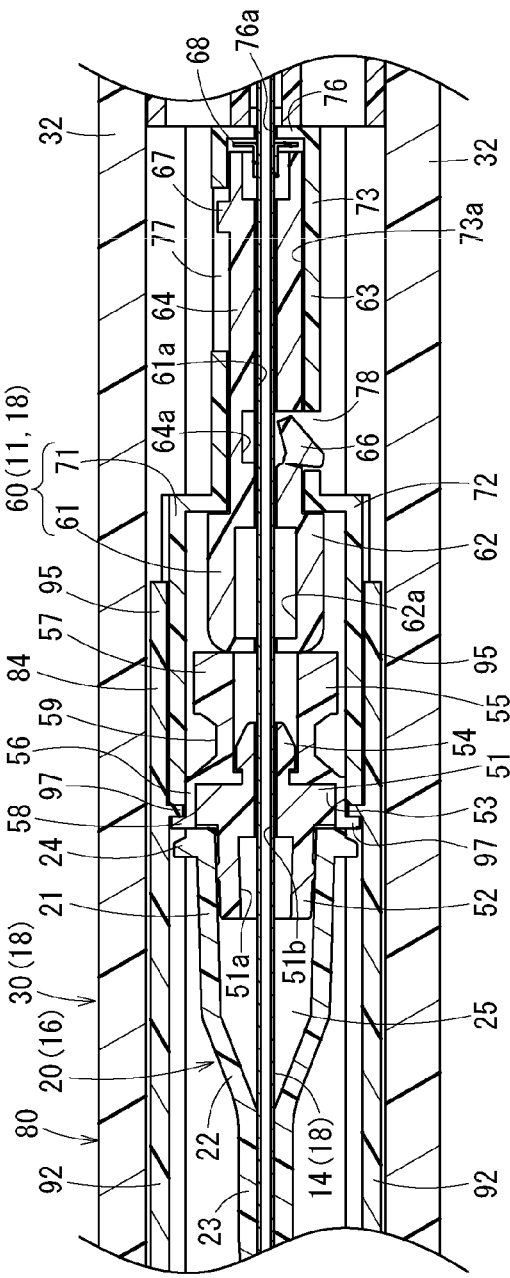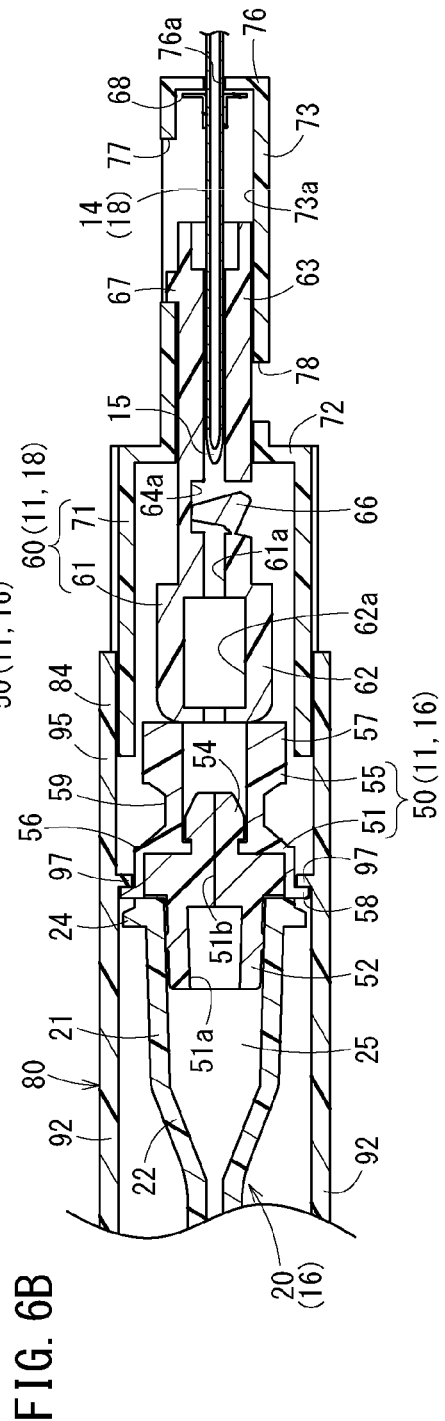

60(18)

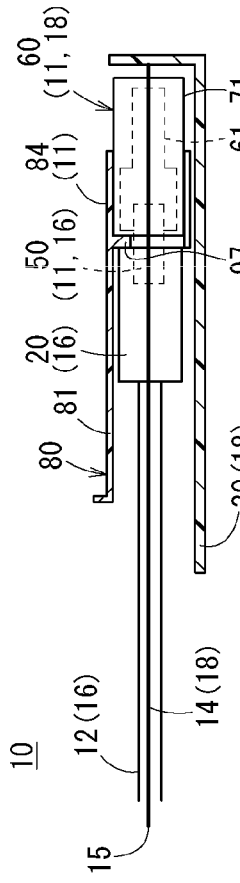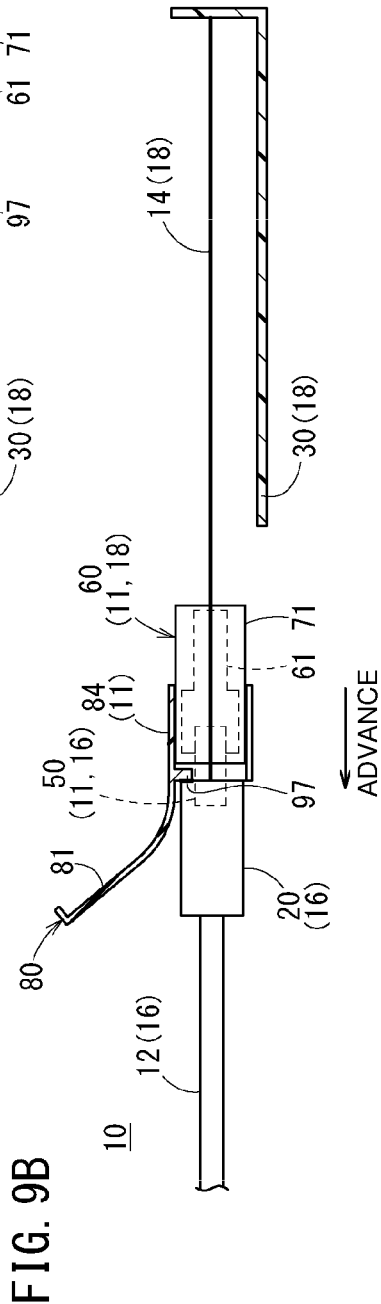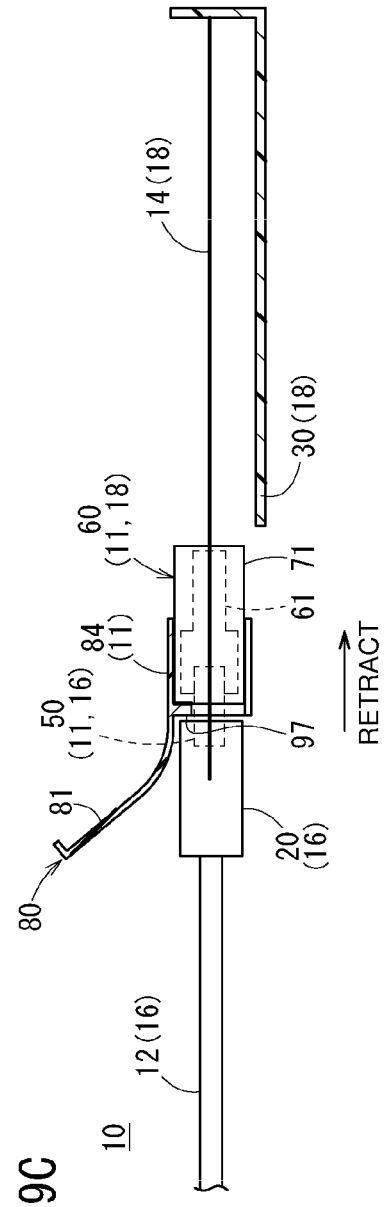

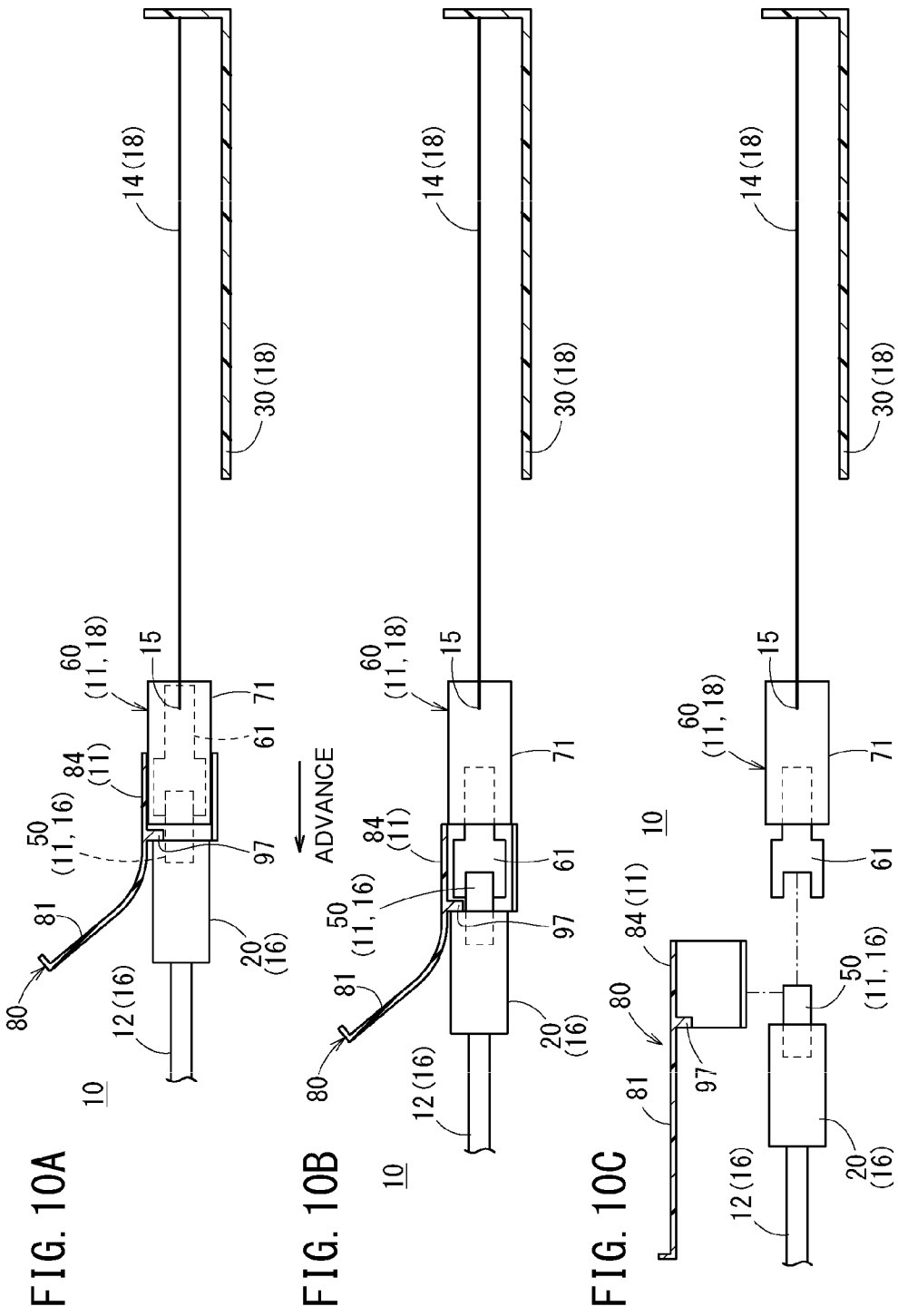

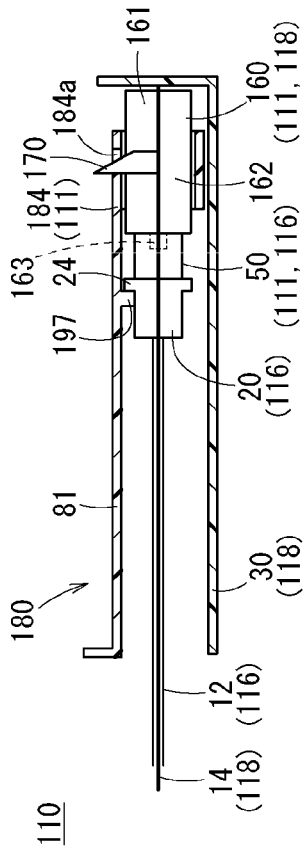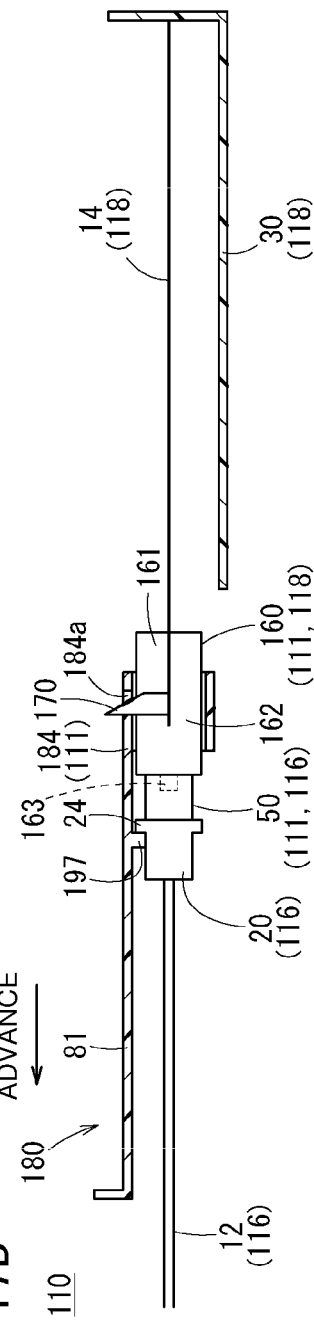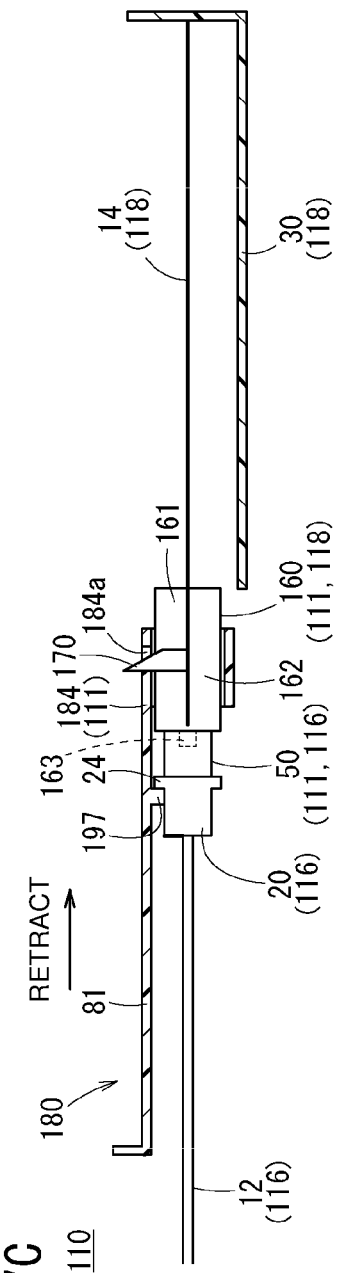

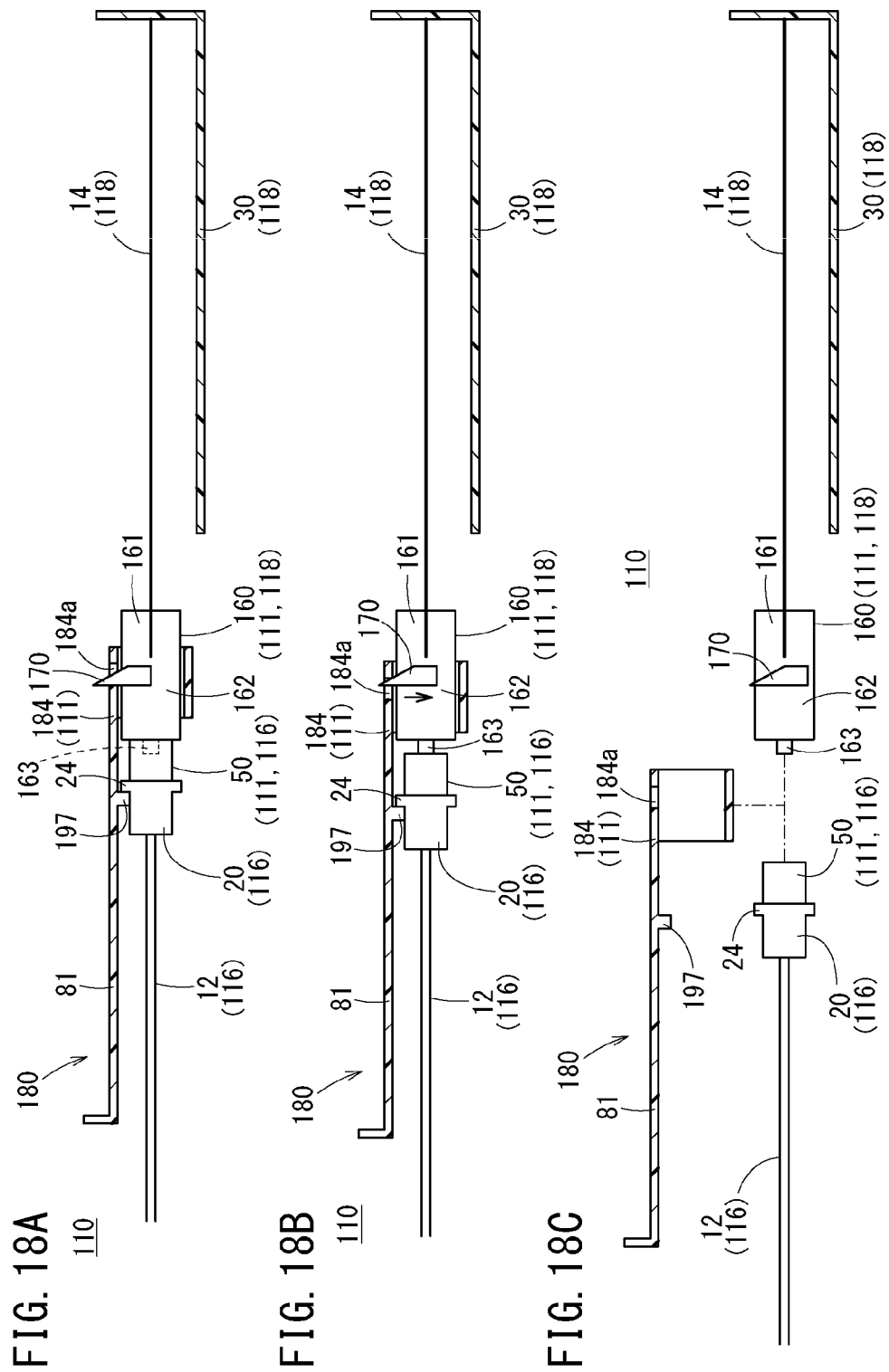

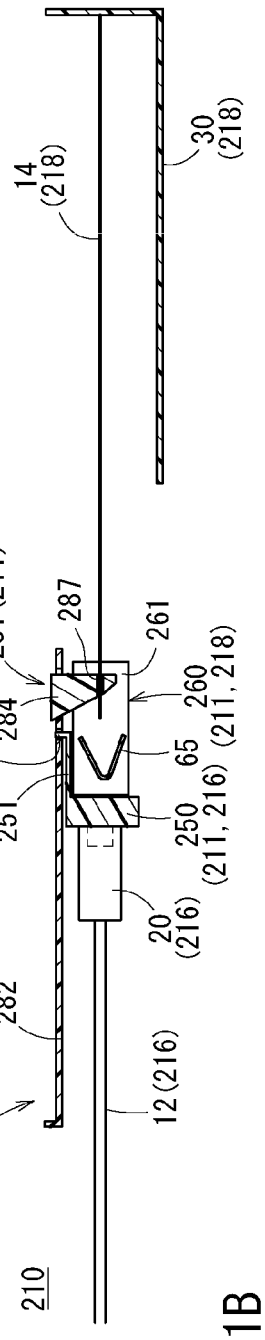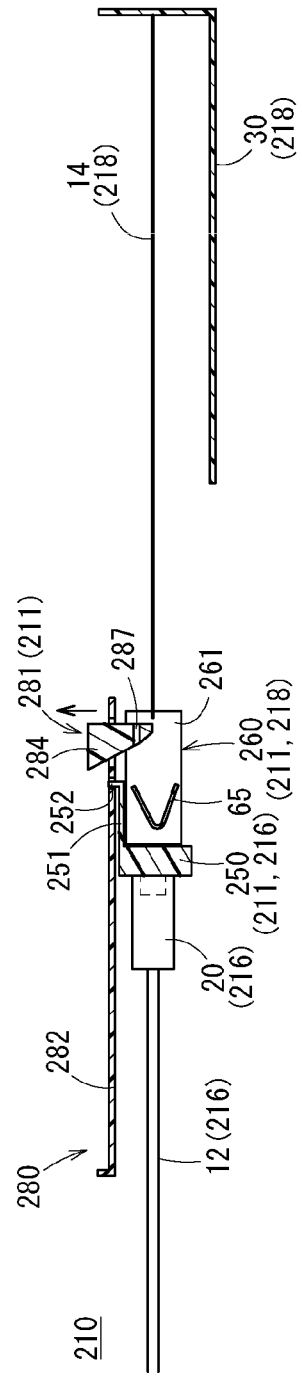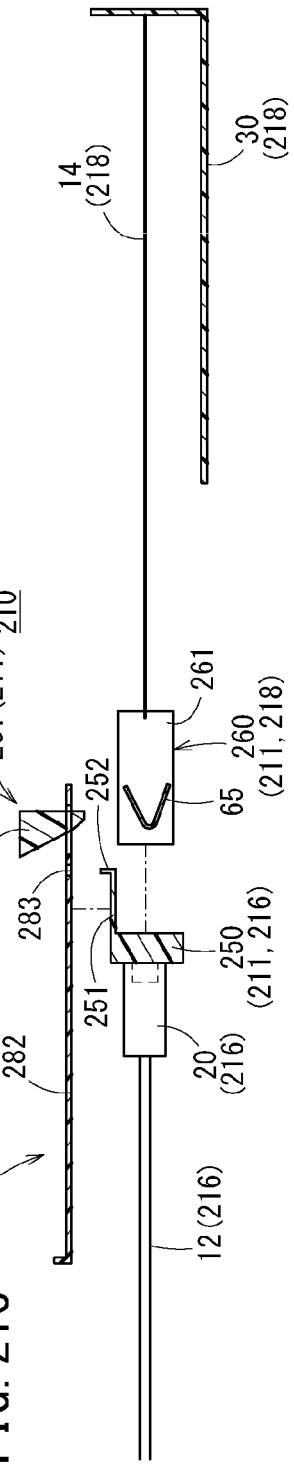

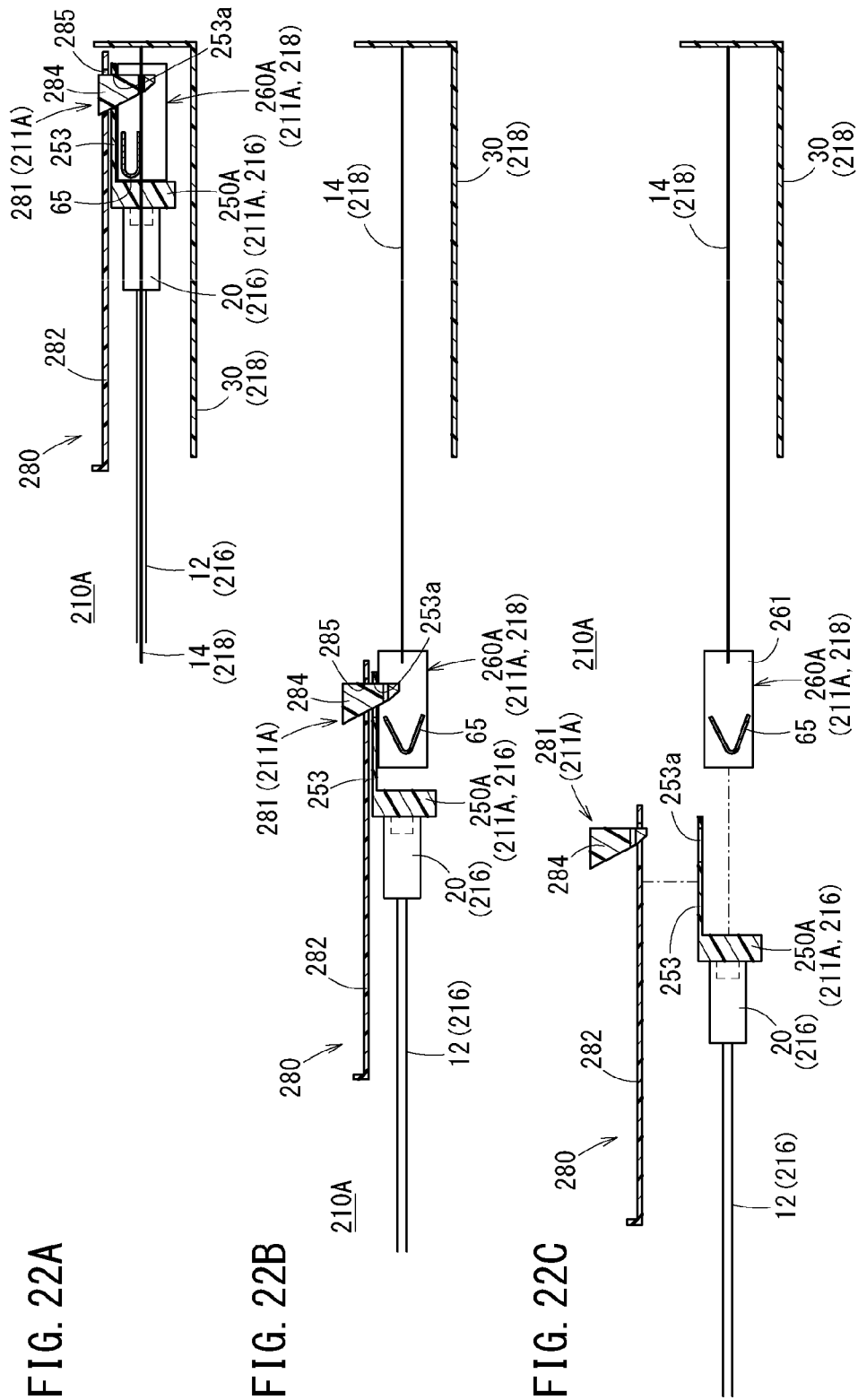

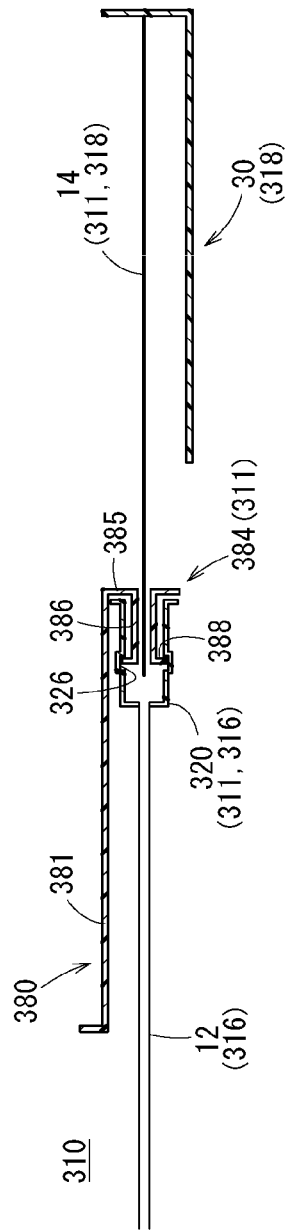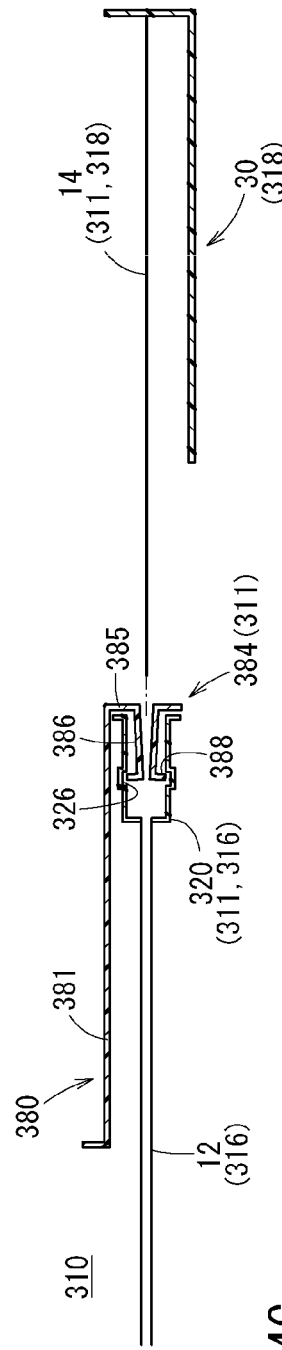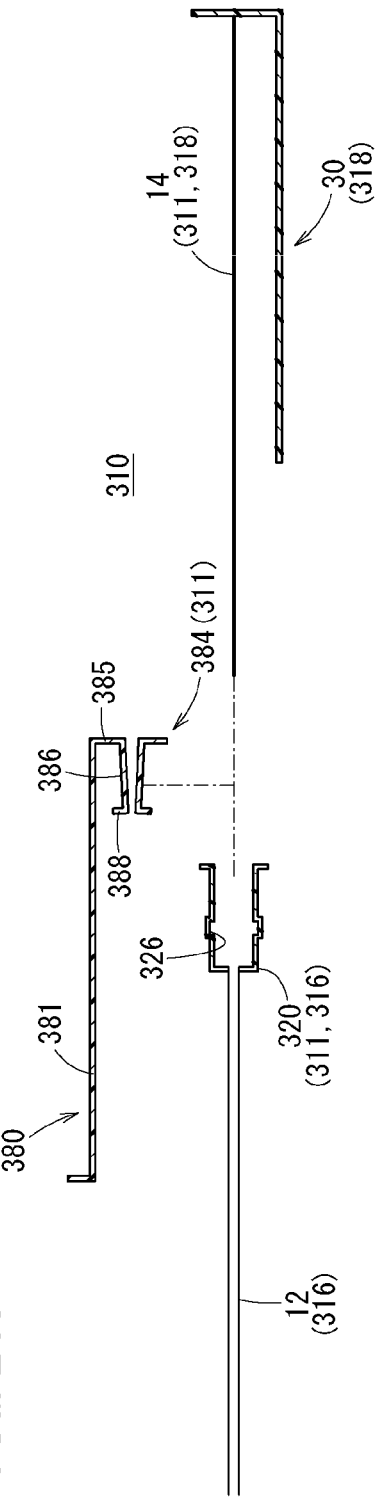

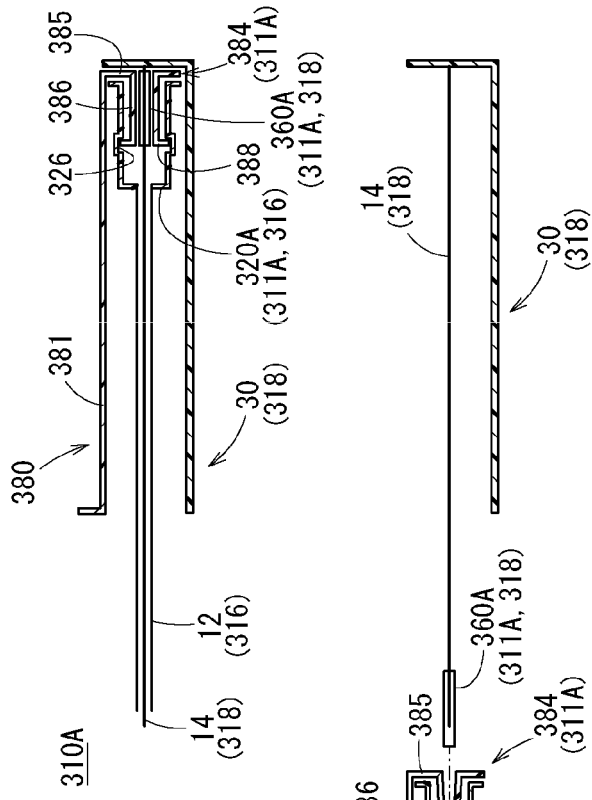
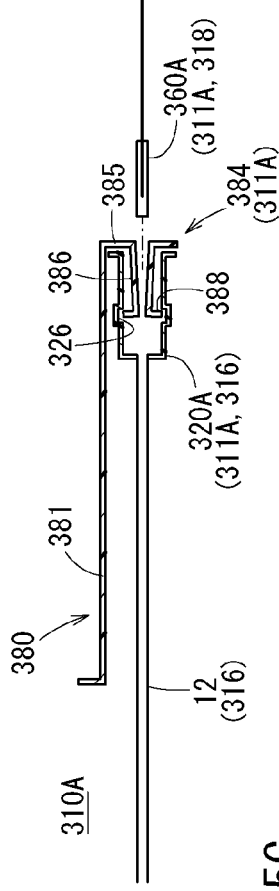
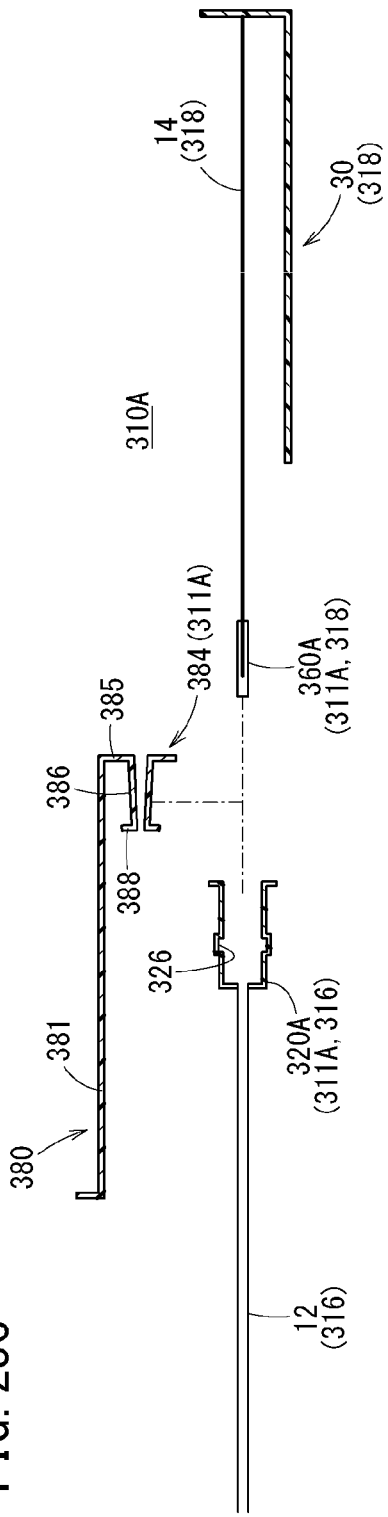
FIG. 25A
FIG. 25B
FIG. 25C

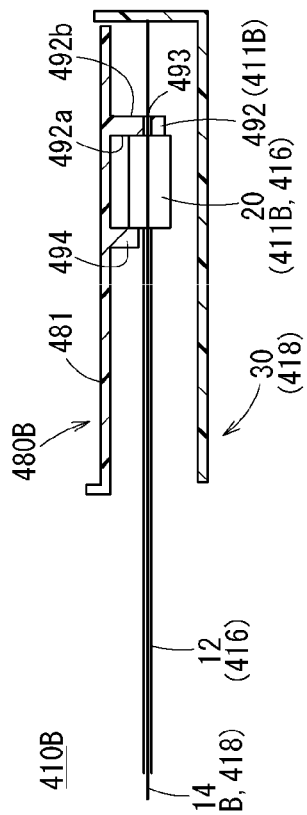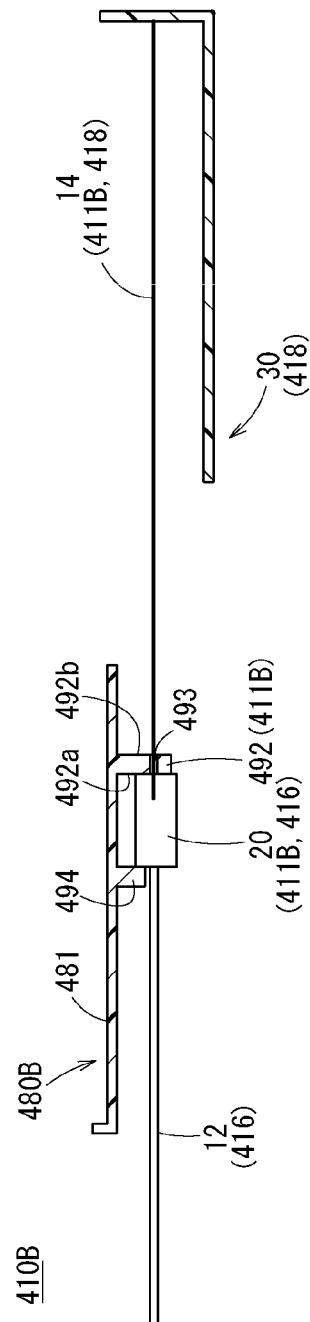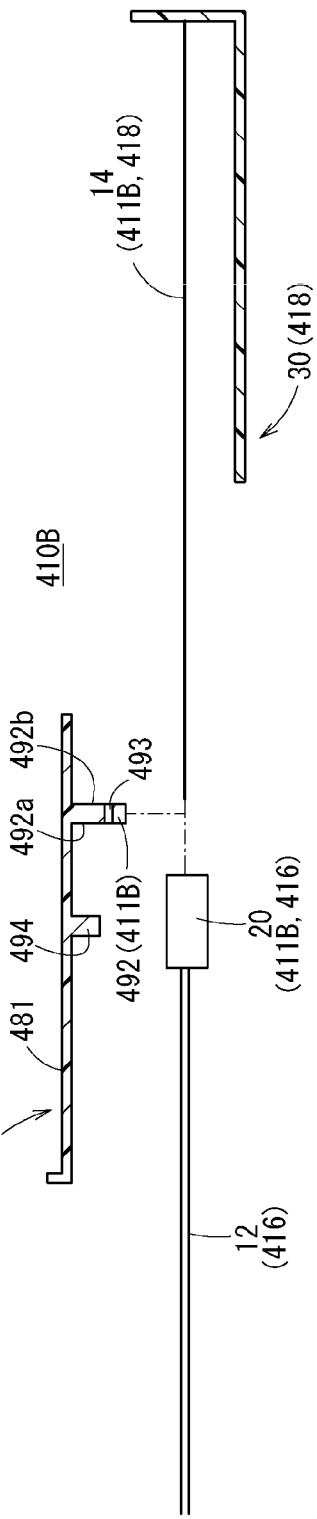

CATHETER ASSEMBLY

CROSS-REFERENCE TO RELATED APPLICATIONS

This is a bypass continuation of PCT Application No. PCT/JP2017/029719, filed on Aug. 21, 2017, which claims priority to Japanese Application No. 2016-164497, filed on Aug. 25, 2016. The contents of these applications are hereby incorporated by reference in their entireties.

BACKGROUND

The present disclosure relates to a catheter assembly that punctures and is indwelled in a blood vessel, for example, when transfusion or the like is performed on a patient.

It is known to use a catheter assembly in construction of an introducing part of an infusion line in the patient at infusion. For example, a catheter assembly disclosed in WO 2011/118643 includes a first assembly including a catheter and a catheter hub for holding a catheter, and a second assembly including an inner needle inserted in the catheter and a needle hub for holding the inner needle. Furthermore, the catheter assembly is provided with a catheter operating member for performing advancement and retraction of the first assembly.

A user, such as a doctor or a nurse, punctures a patient with a double-layered needle having the inner needle inserted in the catheter at the time of use. Then, the catheter operating member relatively advances the first assembly with respect to the second assembly to insert the catheter in the body. Also, the second assembly is retracted relative to the first assembly and separated therefrom. After separation, the first assembly and the catheter operating member are further separated to indwell the first assembly in the patient.

SUMMARY

The catheter assembly firmly connects the first assembly to the catheter operating member in order to stably transmit operating force of the catheter operating member to the first assembly. If the first assembly and the catheter operating member are softly connected, there is a possibility that the first assembly is removed from the catheter operating member during operation.

However, when the first assembly and the catheter operating member are firmly connected to each other, large force is required for separating the first assembly from the catheter operating member when the first assembly is indwelled. For example, at the time of indwelling, while the catheter hub is grasped with one hand, the catheter operating member is grasped with the other hand, and they are separated with force to separate from each other. If such large force is applied, there is a possibility that a position of the catheter is displaced or that the catheter hub is contaminated because of bacteria attached when the user grasps the vicinity of an opening of the catheter hub.

The present invention is achieved in view of the above-described circumstances, and an object thereof is to provide a catheter assembly capable of excellently performing an advancement/retraction operation and indwelling the catheter by easily switching between restriction and allowance of separation of the catheter hub and the catheter operating member.

According to one embodiment, a catheter assembly includes a first assembly including a catheter and a catheter hub that fixes and holds the catheter, a second assembly including an inner needle removably inserted in the catheter and the catheter hub and a needle hub that fixes and holds the inner needle, and a catheter operating member that operates relative movement of the first assembly with respect to the second assembly. And the catheter assembly including a separation restricting mechanism provided separately from the needle hub, in which the separation restricting mechanism restricts separation of the first assembly and the catheter operating member in an inserted state in which the inner needle is inserted in the catheter and allows the separation of the first assembly and the catheter operating member in a non-inserted state in which the inner needle is separate from the catheter.

According to the description above, because the separation restricting mechanism of the catheter assembly is provided separately from the needle hub, the separation of the first assembly and the catheter operating member may be restricted if it is in the inserted state even when the first assembly is separated from the needle hub. Therefore, even when the first assembly is exposed from the needle hub, the connection between the first assembly and the catheter operating member continues, and the operating force of the catheter operating member is surely transmitted to the first assembly. On the other hand, the separation restricting mechanism is easily switched to a state that allows separation of the first assembly and the catheter operating member in the non-inserted state that the inner needle is separated from the catheter. As a result, the catheter operating member and the first assembly may be smoothly separated from each other without the need of large force, and the first assembly may be remained on a patient side.

In this case, the separation restricting mechanism may further allow the separation of the first assembly and the catheter operating member on the basis of a fact that separation of the second assembly and the catheter operating member is restricted in the inserted state and the separation of the second assembly and the catheter operating member is allowed in the non-inserted state.

The catheter assembly may restrict the separation of the first assembly, the second assembly, and the catheter operating member from each other by restricting the separation of the second assembly from and catheter operating member in the inserted state. Also, it is possible to easily separate the first assembly, the second assembly, and the catheter operating member from each other by allowing the separation of the second assembly and the catheter operating member in the non-inserted state.

In addition, the catheter operating member preferably include a connecting unit forming a part of the separation restricting mechanism and directly connecting to the second assembly, and relative movement of the connecting unit in a direction other than an axial direction of the inner needle may be restricted until the inserted state transitions to the non-inserted state.

The relative movement of the catheter assembly in the direction other than the axial direction of the inner needle is restricted by the connecting unit, so that it is possible to easily relatively move the first assembly along an axial center of the inner needle while inhibiting separation of the catheter operating member until the inserted state transitions to the non-inserted state.

Furthermore, the second assembly preferably include an auxiliary member arranged on a side closer to a proximal end than the first assembly and forms another part of the separation restricting mechanism, and the auxiliary member in which the inner needle is inserted so as to be relatively movable may be connected to the connecting unit in the inserted state.

The catheter assembly is provided with the auxiliary member on the side closer to the proximal end than the first assembly and the auxiliary member is connected to the connecting unit, so that the catheter operating member and the auxiliary member (second assembly) may be continuously connected in a satisfactory condition at a position where the auxiliary member is away from the needle hub.

In addition to the above-described configuration, the catheter operating member preferably includes a projection arranged between the first assembly and the auxiliary member.

In the catheter assembly, because the catheter operating member includes the projection, in an advancement operation of the catheter operating member, the projection is pressed against the first assembly and operating force may be surely transmitted to the first assembly. In contrast, in a retraction operation of the catheter operating member, the projection is pressed against the auxiliary member, and the operating force may be surely transmitted to the auxiliary member.

Also, the auxiliary member may include a movable member engaged with the connecting unit in the inserted state and disengaged from the connecting unit by relatively displacing with respect to the auxiliary member in the non-inserted state.

In this manner, because the auxiliary member includes the movable member, this may firmly connect the catheter operating member in the inserted state, and this may be easily separated from the catheter operating member by the displacement of the movable member in the non-inserted state.

Alternatively, the connecting member may include a movable member engaged with the auxiliary member in the inserted state and disengaged from the auxiliary member by relatively displacing with respect to the auxiliary member in the non-inserted state.

With a fact that the connecting unit includes the movable member also, the catheter assembly may easily switch between separation restriction of the catheter operating member and the auxiliary member and separation allowance of the catheter operating member and the auxiliary member.

Furthermore, the connecting unit may be directly connected to the first assembly in the inserted state.

As a result, the catheter assembly may connect the second assembly and the catheter operating member and connect the first assembly, and may easily switch between the separation restriction and the separation allowance of the catheter hub and catheter operating member.

Herein, the separation restricting mechanism preferably allows the separation of the first assembly and the catheter operating member at a stage that a needle tip of the inner needle retracts to a position in which re-exposure is inhibited in the needle hub or in the auxiliary member.

As a result, the catheter assembly may allow the separation of the first assembly and the catheter operating member at a stage of the exposure of the needle tip of the inner needle is inhibited, so that safety at the time of user handling is improved.

In addition, the connecting unit is preferably directly connected to the inner needle so as to be slidable in the catheter hub.

The catheter assembly may easily switch between the separation restriction and the separation allowance of the catheter hub and the catheter operating member even if the connecting unit is directly connected to the inner needle so as to be slidable in the catheter hub.

Alternatively, the connecting unit may also be directly connected to the inner needle so as to be slidable on a side closer to a proximal end than the catheter hub.

The catheter assembly may restrict the separation of the catheter hub and the catheter operating member until the inner needle exits the connecting unit and may easily allow the separation when the inner needle exits the connecting unit even if the connecting unit is directly connected to the inner needle so as to be slidable on the side closer to the proximal end than the catheter hub.

Furthermore, the connecting unit may include an accommodating unit covering an upper portion and a side portion of the catheter hub to accommodate the catheter hub, and a wall portion that is directly connected to the inner needle and comes into contact with the catheter hub at the time of relative movement of the catheter operating member.

In this manner, because the connecting unit covers an upper portion and a side portion of the catheter hub, it is possible to inhibit the needle hub and the catheter hub from coming into contact with each other when the catheter operating member moves, thereby suppressing the catheter hub from shaking, so that the first assembly may advance in a more satisfactory condition.

Furthermore, an inner peripheral surface forming the accommodating unit of the connecting unit is preferably separated from an outer peripheral surface of the catheter hub in a radial direction.

In the catheter assembly, because the inner peripheral surface of the connecting unit is separated from the outer peripheral surface of the catheter hub, when the inner needle is separated, the catheter hub may be separated from the catheter operating member without force.

According to the present invention, the catheter assembly is such that the catheter may be advanced/retracted and indwelled in a satisfactory condition by easily switching between restriction and allowance of the separation of the catheter hub and the catheter operating member.

BRIEF DESCRIPTION OF THE DRAWINGS

FIG. 6A is a plan sectional view illustrating the separation restricting mechanism in FIG. 3, and FIG. 6B is a plan sectional view illustrating the separation restricting mechanism in FIG. 4.

FIG. 9A is a first illustrative view schematically illustrating operation of the catheter assembly in FIG. 1, FIG. 9B is a second illustrative view of operation at the time of an advancement operation of the catheter assembly in FIG. 1, and FIG. 9C is a third illustrative view of operation at the time of a retraction operation of the catheter assembly in FIG. 1.

FIG. 10A is a fourth illustrative view of operation following FIG. 9B, FIG. 10B is a fifth illustrative view of operation following FIG. 10A, and FIG. 10C is a sixth illustrative view of operation following FIG. 10B.

FIG. 17A is a first illustrative view schematically illustrating operation of the catheter assembly in FIG. 13, FIG. 17B is a second illustrative view of operation at the time of an advancement operation of the catheter assembly in FIG. 13, and FIG. 17C is a third illustrative view of operation at the time of a retraction operation of the catheter assembly in FIG. 13.

FIG. 18A is a fourth illustrative view of operation following FIG. 17B, FIG. 18B is a fifth illustrative view of operation following FIG. 18A, and FIG. 18C is a sixth illustrative view of operation following FIG. 18B.

FIG. 21A is a first illustrative view illustrating operation of the catheter assembly in FIG. 20B, FIG. 21B is a second illustrative view of operation following FIG. 21A, and FIG. 21C is a third illustrative view of operation following FIG. 21B.

FIG. 22A is a first side sectional view schematically illustrating a catheter assembly according to a third variation, FIG. 22B is a second side sectional view of operation following FIG. 22A, and FIG. 22C is a third side sectional view of operation following FIG. 22B.

FIG. 24A is a first illustrative view illustrating operation of the catheter assembly in FIG. 23B, FIG. 24B is a second illustrative view of operation following FIG. 24A, and FIG. 24C is a third illustrative view of operation following FIG. 24B.

FIG. 25A is a first side sectional view schematically illustrating a catheter assembly according to a fourth variation, FIG. 25B is a second side sectional view of operation following FIG. 25A, and FIG. 25C is a third side sectional view of operation following FIG. 25B.

FIG. 30A is a first side sectional view schematically illustrating a catheter assembly according to a sixth variation, FIG. 30B is a second side sectional view of operation following FIG. 30A, and FIG. 30C is a third side sectional view of operation following FIG. 30B.

DETAILED DESCRIPTION

Preferred embodiments of a catheter assembly according to the present invention are hereinafter described in detail with reference to the accompanying drawings.

The catheter assembly according to the present invention is used, for example, to form an introducing unit of an infusion agent or a blood product when performing infusion, transfusion or the like on a patient (living body). The catheter assembly may be configured as a catheter longer in length than a peripheral venous catheter (for example, central venous catheter, PICC, midline catheter and the like). Note that the catheter assembly may also be configured as the peripheral venous catheter. The catheter assembly is not limited to a venous catheter and may be configured as an arterial catheter such as a peripheral arterial catheter.

First Embodiment

Figure 1:
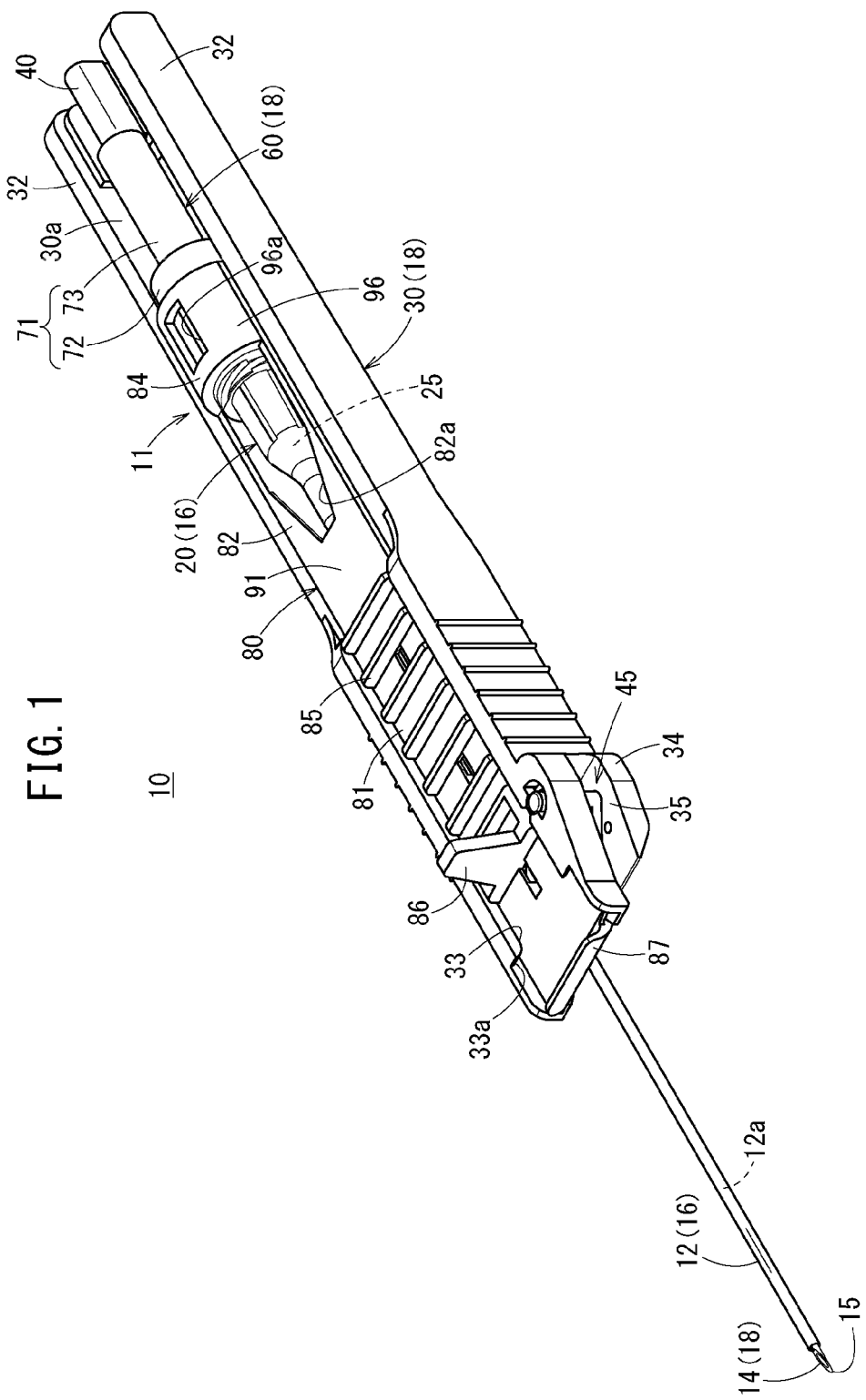
FIG. 1 is a perspective view illustrating a catheter assembly according to a first embodiment of the present invention.
Figure 2:
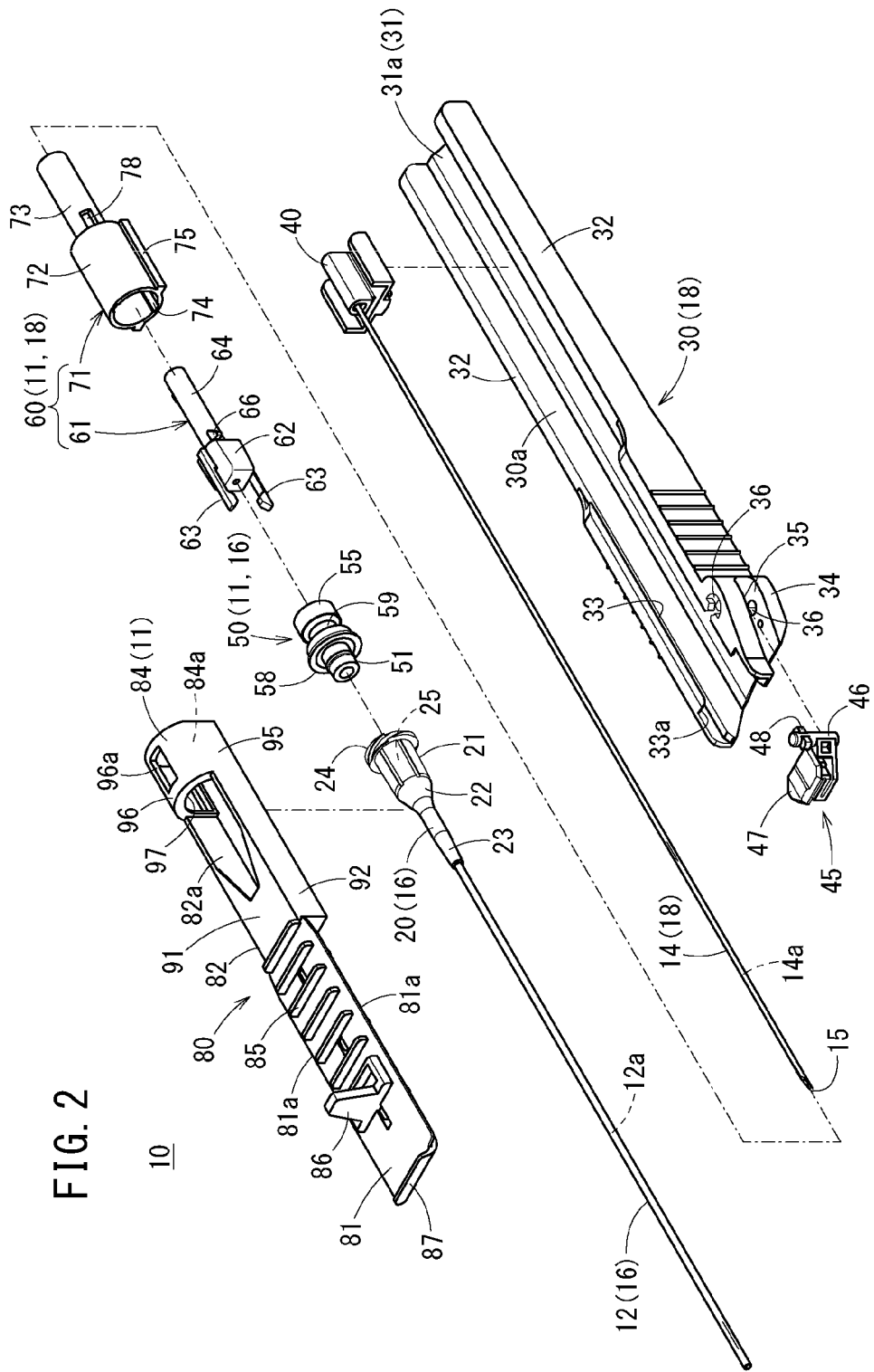
FIG. 2 is an exploded perspective view of the catheter assembly in FIG. 1.

As illustrated in FIGS. 1 and 2, a catheter assembly 10 according to a first embodiment is provided with a catheter 12, an inner needle 14, a catheter hub 20, and a housing 30 (needle hub). The catheter 12 and the catheter hub 20 are connected and fixed to each other to form a first assembly 16. The inner needle 14 and the housing 30 are connected and fixed to each other to form a second assembly 18. The first assembly 16 also includes a valve mechanism 50 that blocks a proximal end of the catheter hub 20. The second assembly 18 includes a safety mechanism 60 (auxiliary member) that accommodates a needle tip 15 of the inner needle 14 so as not to be exposed after use. Furthermore, the catheter assembly 10 is provided with a catheter operating member 80 that operates relative movement of the first assembly 16 with respect to the second assembly 18.

The first assembly 16 is an instrument separated from the second assembly 18 and indwelled in a patient when the catheter assembly 10 is used. For example, in a state in which the catheter 12 is inserted in a blood vessel of the patient, the first assembly 16 is such that a proximal end portion of the catheter 12 and the catheter hub 20 are exposed on the skin of the patient and the exposed portion is adhered with tape or the like. Thereafter, the user removes the valve mechanism 50 from the catheter hub 20, and connects an infusion tube not illustrated to the proximal end of the catheter hub 20. As a result, a infusion agent or the like is supplied from the infusion tube to the patient via the first assembly 16.

The catheter 12 has moderate flexibility and is provided with a lumen 12a formed along an axial center thereof so as to penetrate the same. The lumen 12a is formed to have such a diameter that the inner needle 14 may be accommodated therein and the infusion agent or the like may flow therethrough. The proximal end of the catheter 12 is fixed to a distal end in the catheter hub 20 by an appropriate fixing method such as fusion, adhesion, or caulking. A length of the catheter 12 may be designed according to a purpose and various conditions; for example, this is set to approximately 14 to 500 mm, or approximately 30 to 400 mm, or approximately 76 to 200 mm.

As components of the catheter 12, soft resin materials are preferably used, and examples thereof include, for example, fluorine resins such as polytetrafluoroethylene (PTFE), an ethylene tetrafluoroethylene copolymer (ETFE), and a perfluoroalkoxy fluorine resin (PFA), olefin resins such as polyethylene and polypropylene or a mixture thereof, polyurethane, polyester, polyamide, a polyether nylon resin, a mixture of an olefin resin and an ethylene/vinyl acetate copolymer and the like.

The catheter hub 20 is harder than the catheter 12 and is formed into a cylindrical shape elongated in an axial direction. In detail, a large-diameter portion 21 on a proximal end side, a transition portion 22 connected to the large-diameter portion 21 and tapered in a distal end direction, and a small-diameter portion 23 connected to the transition portion 22 and extending in the distal end direction are included. A flange 24 projecting radially outward and circumferentially circling is formed on a proximal end side outer peripheral surface of the large-diameter portion 21.

Figure 3:
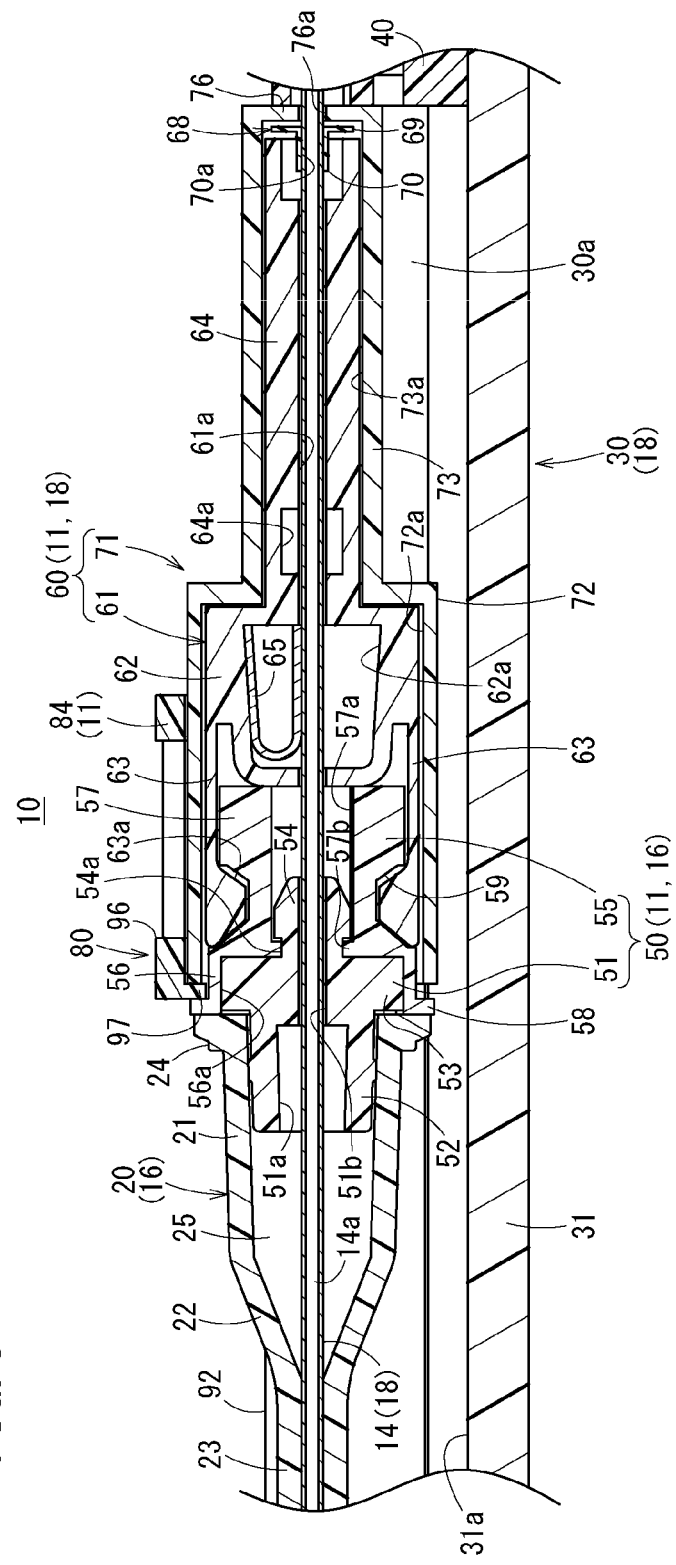
FIG. 3 is a side sectional view illustrating a separation restricting mechanism in an inserted state of the catheter assembly in FIG. 1.

As illustrated in FIG. 3, the catheter hub 20 has a hollow portion 25 communicated with the lumen 12a of the catheter 12. The hollow portion 25 has a tapered shape corresponding to outer shapes of the large-diameter portion 21, the transition portion 22, and the small-diameter portion 23. The catheter 12 is inserted and fixed to the hollow portion 25 of the small-diameter portion 23. In the hollow portion 25 of the large-diameter portion 21, the valve mechanism 50 is inserted in an initial state. Note that, although not illustrated, the hollow portion 25 may accommodate a hemostasis valve that inhibits backflow of blood at the time of puncture with the inner needle 14, a plug that penetrates the hemostatic valve in accordance with insertion of a connector of the infusion tube to enable infusion and the like.

Components of the catheter hub 20 are not especially limited; for example, thermoplastic resins such as polypropylene, polycarbonate, polyamide, polysulfone, polyallylate, and a methacrylate-butylene-styrene copolymer may be used.

As illustrated in FIGS. 2 and 3, the valve mechanism 50 has a function of blocking the proximal end of the catheter hub 20, thereby improving a sealing performance and a sanitary property of the first assembly 16 in the initial state, and inhibiting leakage of the blood flowing into the hollow portion 25 from the lumen 12a of the catheter 12. The valve mechanism 50 includes a valve main body 51 mainly made of an elastic material and a connector 55 connected and fixed to a proximal end side of the valve main body 51 made of a resin material harder than that of the valve main body 51.

The valve main body 51 includes an inserted portion 52 inserted in the hollow portion 25 of the catheter hub 20, a disk-shaped base portion 53 connected to a proximal end of the inserted portion 52, and a coupling projection 54 projecting from a central portion of the base portion 53 in a proximal end direction. Also, the valve main body 51 has a hole 51a inside the inserted portion 52, and has a valve hole 51b communicated with the hole 51a and penetrating in an axial direction inside the base portion 53 and the coupling projection 54. The inner needle 14 is arranged in the hole 51a and the valve hole 51b in the initial state. The valve hole 51b self-closes as the inner needle 14 is removed.

The inserted portion 52 is elastically deformed in a state of being inserted in the hollow portion 25 and is brought into close contact with an inner surface of the large-diameter portion 21 with appropriate sealing force. The base portion 53 projects radially outward of the inserted portion 52 to close the proximal end of the catheter hub 20. The coupling projection 54 is a portion for coupling the valve main body 51 to the connector 55 and is provided with an annular concave portion 54a on an outer peripheral surface near the base portion 53.

The connector 55 is provided with a distal end tubular portion 56 having a distal end accommodating unit 56a in which the base portion 53 is accommodated and a proximal end tubular portion 57 having a proximal end accommodating unit 57a in which the coupling projection 54 is accommodated. An outer annular convex portion 58 projecting radially outward is provided on a distal end side outer peripheral surface of the distal end tubular portion 56. In the initial state, the outer annular convex portion 58 is arranged in the vicinity of the proximal end of the catheter hub 20 (flange 24) and serves as a position for receiving operating force when the catheter operating member 80 advances.

An inner annular convex portion 57b projecting radially inward is provided on a distal end side inner peripheral surface of the proximal end tubular portion 57 forming the proximal end accommodating unit 57a. The inner annular convex portion 57b is engaged with an annular concave portion 54a of the coupling projection 54 inserted in the proximal end accommodating unit 57a to firmly couple the valve main body 51 and the connector 55. Furthermore, on an outer peripheral surface of the proximal end tubular portion 57, a constricted portion 59 that is tapered radially inward from front and rear outer peripheral surfaces is provided. In the initial state, an arm 63 of the safety mechanism 60 to be described later is caught by the constricted portion 59 and the arm 63 is detached during use, so that the valve mechanism 50 and the safety mechanism 60 may be separated (refer also to FIG. 4).

With reference to FIG. 1 again, the second assembly 18 is an instrument that forms a wound and insertion guide the catheter 12 while the catheter assembly 10 is used and is separated from the first assembly 16 to be discarded when the first assembly 16 is indwelled.

The inner needle 14 of the second assembly 18 is formed into a hollow tube having rigidity capable of puncturing the skin of a living body. The inner needle 14 is formed to be longer than an entire length of the catheter 12, and is provided with a sharp needle tip 15 at a distal end thereof and a needle hole 14a inside thereof in an axial direction. In the initial state illustrated in FIG. 1, the inner needle 14 penetrates through the lumen 12a of the catheter 12 and the hollow portion 25 of the catheter hub 20 to form a multi-layered needle and exposes the needle tip 15 from the distal end of the catheter 12. Note that it is possible to cut out a part of an outer peripheral surface of the inner needle 14 in the axial direction to form a groove, or a lateral hole communicated with the needle hole 14a may be provided. The inner needle 14 may also be a solid needle.

The inner needle 14 may be formed of, for example, a metal material such as stainless steel, aluminum or an aluminum alloy, and titanium or a titanium alloy, a hard resin, ceramics and the like. The inner needle 14 is firmly fixed to a needle holding member 40 of the housing 30 by an appropriate fixing method (fusion, adhesion, insert molding and the like).

In the initial state, the housing 30 has an elongated bowl shape for accommodating the first assembly 16, the inner needle 14, the safety mechanism 60, and the catheter operating member 80, and forms a grip used when the user pierces with the multi-layered needle. In detail, as illustrated in FIG. 2, a lower wall 31 having a guide groove 31a in a central portion in a width direction (lateral direction) and a pair of side walls 32 projecting upward from both sides of the lower wall 31 are provided (refer also to FIG. 5), and an accommodating space 30a is formed between the lower wall 31 and the pair of side walls 32. In addition, the housing 30 is provided with the needle holding member 40 for holding the inner needle 14 on a proximal end side, and a supporting member 45 for supporting the multi-layered needle from below on a distal end side.

The guide groove 31a of the lower wall 31 is concave downward in an arc shape, and the safety mechanism 60 is slidably arranged therein. In addition, in the guide groove 31a on the proximal end side, a mounting hole not illustrated on which the needle holding member 40 is mounted is provided. Note that the needle holding member 40 may also be formed integrally with the housing 30.

The pair of side walls 32 extends in parallel in a longitudinal direction together with the lower wall 31 with a proximal end side and an intermediate side formed to have a certain height and a distal end side formed higher than the intermediate side. A groove-shaped rail portion 33 is provided on an inner surface in an upper part on the distal end side of each side wall 32. Each of the pair of rail portions 33 is connected to an open guiding unit 33a in the upper part on the distal end side of each side wall 32 and linearly extends in each side wall 32 in the proximal end direction, and is connected to an upper surface on the intermediate side of each side wall 32. The pair of rail portions 33 accommodates a side edge 81a of the catheter operating member 80 and guides advancement and retraction of the catheter operating member 80. In addition, the open guiding unit 33a is cut out on the upper side of the housing 30, thereby allowing the catheter operating member 80 to bend.

Figure 5:
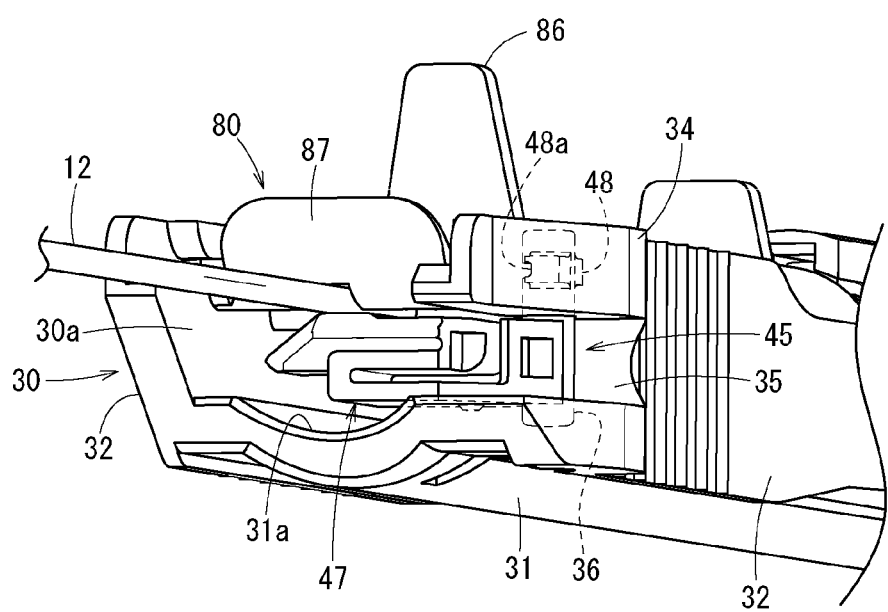
FIG. 5 is a perspective view illustrating a distal end side of a grip in FIG. 1.

Furthermore, as illustrated in FIGS. 2 and 5, one side wall 32 of the pair of side walls 32 has a bulging portion 34 bulging outward in the width direction. Between the lower wall 31 of the bulging portion 34 and the rail portion 33, an arranging concave portion 35 is cut out from the distal end of the side wall 32 in the proximal end direction. In addition, an upper and lower pair of bearing holes 36 for rotatably attaching the supporting member 45 is provided on the lower wall 31 and the side wall 32 at a position where the arranging concave portion 35 is formed.

The supporting member 45 includes an axial rod 46 rotatably attached to the pair of bearing holes 36, a supporting main body 47 projecting from an axial center of the axial rod 46 in a direction orthogonal to this, and an upper projection 48 provided at an upper end of the axial rod 46. The supporting main body 47 is formed into a crank shape as seen from the front and elastically supports the catheter 12. The upper projection 48 has a guide concave portion 48a connected to the rail portion 33 on an inner side in a width direction and the side edge 81a of the catheter operating member 80 is arranged in the guide concave portion 48a in the initial state.

As illustrated in FIGS. 1 and 5, in the initial state, the supporting member 45 is such that the supporting main body 47 is arranged on an inner side of the side walls 32 (under the catheter 12) by the axial rod 46 to stand by so as to be able to support the catheter 12. At that time, the side edge 81a (refer to FIG. 2) of the catheter operating member 80 is located in the guide concave portion 48a of the upper projection 48 to restrict the rotation of the axial rod 46. In use, when downward pressing force is applied from the user to the catheter operating member 80, the supporting main body 47 supports the catheter 12 from below and suppresses bending of the catheter 12.

As the catheter operating member 80 advances, the side edge 81a of the catheter operating member 80 exits the guide concave portion 48a, and a side plate 92 of the catheter operating member 80 comes into contact with the supporting main body 47 and rotate the supporting main body 47 toward the outside of the side wall 32. As a result, the supporting member 45 smoothly delivers the first assembly 16, the safety mechanism 60, and the catheter operating member 80 from the housing 30.

The resin material forming the housing 30 (including the needle holding member 40 and the supporting member 45) is not especially limited, and the materials cited with the catheter hub 20 may be appropriately selected, for example. No that, in the catheter assembly 10 according to this embodiment, the safety mechanism 60 and the catheter operating member 80 are exposed on an upper side. Alternatively, the catheter assembly 10 may be configured to cover the catheter operating member 80, the safety mechanism 60 and the like by forming an upper wall on or attaching a lid to the housing 30.

On the other hand, the safety mechanism 60 in which the inner needle 14 is arranged so as to penetrate the same in the initial state accommodates the needle tip 15 moving as the inner needle 14 is withdrawn from the first assembly 16 and inhibits re-exposure of the needle tip 15. As illustrated in FIGS. 2 to 4, 6A, and 6B, the safety mechanism 60 is formed into a telescope shape provided with an inner tube 61 and an outer tube 71 that accommodates the inner tube 61 so as to be relatively movable.

The inner tube 61 having a distal end located on a side closer to the proximal end than a distal end of the outer tube 71 in the initial state connects to hold the valve mechanism 50. The inner tube 61 is provided with a box body 62, a pair of arms 63 integrally formed on side surfaces of the box body 62, and an inner tubular portion 64 extending from the box body 62 in the proximal end direction. An insertion hole 61a through which the inner needle 14 passes is formed to penetrate inside the box body 62 and the inner tubular portion 64.

The box body 62 is formed into a rectangular parallelepiped shape having rounded corners in four directions, and a cavity 62a communicated with the insertion hole 61a is provided therein. In the cavity 62a, a shutter 65 for inhibiting the re-exposure of the needle tip 15 is arranged. The shutter 65 is formed into a U-shaped flat spring in a side sectional view. In a state in which the inner needle 14 is arranged in the cavity 62a, the shutter 65 is accommodated in an elastically deformed state in a space above the inner needle 14, and ends on a side opposite to a U-shaped curved portion are brought closer to each other. When the needle tip 15 of the inner needle 14 retracts toward the proximal end than the shutter 65, the shutter 65 resiliently restores and opens in the cavity 62a, so that this faces the needle tip 15 of the inner needle 14 in a planar manner.

The pair of arms 63 is coupled to the side surfaces in vertical direction of the box body 62 and extends in the distal end direction above and below the box body 62. Hooks 63a projecting inward in a width direction are provided inside distal ends of the arms 63 in an extending direction. Each arm 63 is shaped so that the hook 63a expands outward in the width direction in a natural state in which external force does not act. In contrast, each arm 63 is elastically pressed so that the hook 63a tilts inward by the outer tube 71, and is caught by the constricted portion 59 of the valve mechanism 50 in the initial state (the state in which the inner tube 61 is accommodated in the outer tube 71).

Figure 7:
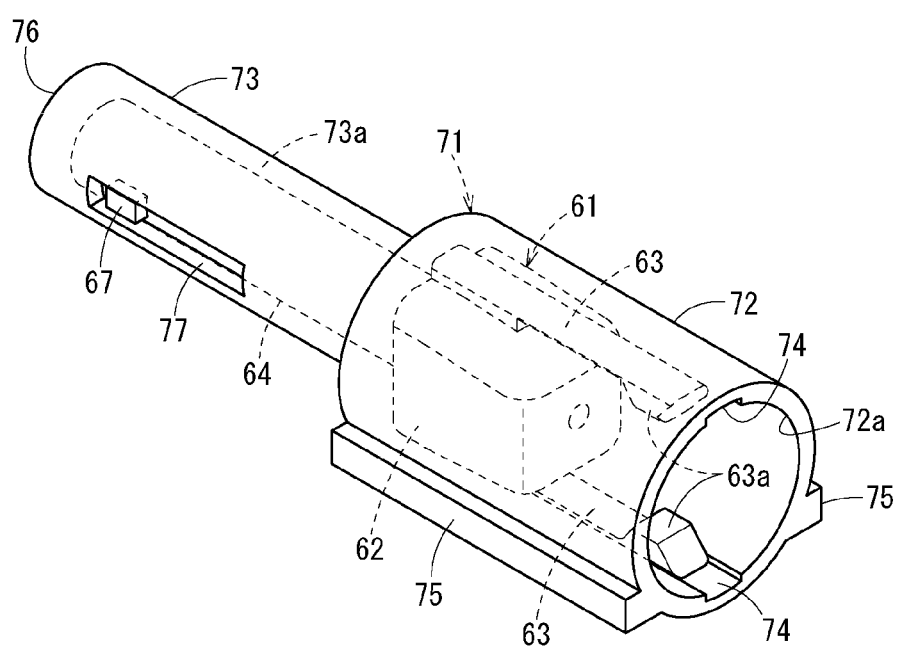
FIG. 7 is an enlarged perspective view of a safety mechanism of the catheter assembly in FIG. 1.

On the other hand, the inner tubular portion 64 of the inner tube 61 is formed into a cylindrical shape that may be accommodated in an outer tubular side hollow portion 73a of the outer tube 71. As illustrated in FIGS. 6A and 6B, a stopper 66 that inhibits separation of the inner tube 61 and the outer tube 71 in the initial state and an allowance space 64a communicated with the insertion hole 61a in which the stopper 66 is arranged so as to be displaced are provided near a distal end of the inner tubular portion 64 (position in the vicinity of the box body 62). As illustrated in FIG. 7, a separation restricting convex portion 67 projecting radially outward is provided on a proximal end side outer peripheral surface of the inner tubular portion 64.

Furthermore, as illustrated in FIG. 3, the insertion hole 61a of the inner tubular portion 64 is formed somewhat larger in diameter on the proximal end side, and a retaining member 68 is accommodated on the proximal end side of the insertion hole 61a and the outer tubular side hollow portion 73a of the outer tube 71. The retaining member 68 has a convex shape having a disk-shaped collar portion 69 in a side sectional view and a projecting tube 70 projecting from the collar portion 69 in the distal end direction. In the projecting tube 70, a hole 70a in which the inner needle 14 is movably arranged is provided.

Herein, an outer shape of the inner needle 14 is gradually made thicker (wider) from a body portion toward the needle tip 15, and a width in the vicinity of the needle tip 15 is wider than a diameter of the hole 70a. Therefore, when the inner needle 14 retracts relative to the retaining member 68, the outer peripheral surface thereof in the vicinity of the needle tip 15 is caught by the projecting tube 70 of the retaining member 68 and removal from the retaining member 68 is inhibited.

In contrast, the outer tube 71 is provided with an accommodating body 72 and an outer tubular portion 73 extending from the accommodating body 72 in the proximal end direction. The accommodating body 72 is formed into a cylindrical shape larger than the box body 62 of the inner tube 61. A cylindrical arranging space 72a in which a part of the valve mechanism 50 and the distal end side of the inner tube 61 (the box body 62, the pair of arms 63 and the like) are arranged in the initial state is provided inside the accommodating body 72.

As illustrated in FIG. 7, sliding grooves 74 parallelly extending in an axial direction of the accommodating body 72 in which the pair of arms 63 is slidably arranged are provided in upper and lower positions on an inner surface of the accommodating body 72 forming the arranging space 72a. Furthermore, on an outer peripheral surface of the accommodating body 72, a pair of projected strips 75 projecting outward in a width direction is provided. The pair of projected strips 75 is located on a side lower than an axial center of the accommodating body 72 (closer to the lower wall 31 of the housing 30) and projects in directions opposite to each other and linearly extends in the axial direction of the accommodating body 72.

The outer tubular portion 73 is formed to be longer than the inner tubular portion 64 of the inner tube 61 and provided with the outer tubular side hollow portion 73a communicated with the arranging space 72a and extending in the axial direction. A rear wall 76 surrounding the outer tubular side hollow portion 73a is provided on a proximal end of the outer tubular portion 73 and a proximal end opening 76a in which the inner needle 14 is inserted is formed in a central portion of the rear wall 76. The collar portion 69 of the retaining member 68 is formed to have a diameter larger than that of the insertion hole 61a of the inner tube 61 and the proximal end opening 76a of the outer tube 71 and is inhibited from dropping from the outer tube 71.

As illustrated in FIGS. 6A and 6B, an elongated hole 77 communicated with the outer tubular side hollow portion 73a and extending in the axial direction of the outer tubular portion 73 is formed on an outer peripheral surface on a proximal end side of the outer tubular portion 73. The elongated hole 77 in which a separation restricting convex portion 67 of the inner tube 61 is arranged inhibits the inner tube 61 from dropping from the outer tube 71 and defines a range of relative movement of the inner tube 61 with respect to the outer tube 71. A stopper window 78 communicated with the outer tubular side hollow portion 73a and facing the allowance space 64a of the inner tube 61 in the initial state is provided on the distal end side outer peripheral surface of the outer tubular portion 73.

As illustrated in FIG. 6A, in the initial state, the safety mechanism 60 is such that the stopper 66 is arranged in the stopper window 78 of the outer tube 71 and is inhibited from displacing inward by the inner needle 14 inserted in the allowance space 64a of the inner tube 61. Therefore, the stopper 66 is caught by the outer tube 71 to restrict the relative movement of the inner tube 61 with respect to the outer tube 71. On the other hand, as illustrated in FIG. 6B, when the needle tip 15 of the inner needle 14 moves toward the proximal end than the stopper 66, the stopper 66 may move in the allowance space 64a. Therefore, the inner tube 61 becomes movable relative to the outer tube 71, and when the inner tube 61 advances, the stopper 66 pushed by the outer tube 71 faces the insertion hole 61a in the allowance space 64a.

With reference to FIGS. 1 and 2 again, the catheter operating member 80 is operated by the user to relatively advance and retract the first assembly 16 with respect to the inner needle 14 and the housing 30. Especially, the catheter operating member 80 is mounted on the safety mechanism 60 connecting the first assembly 16 and is configured to directly hold the catheter 12 in the initial state. Specifically, the catheter operating member 80 includes an operating plate 81 extending in a longitudinal direction of the housing 30, a hub arranging unit 82 coupled to a proximal end of the operating plate 81 in which the catheter hub 20 is arranged, and a connecting unit 84 coupled to a proximal end of the hub arranging unit 82 to accommodate the safety mechanism 60.

The operating plate 81 is a portion that is directly operated with a finger of the user placed thereon. A pair of side edges 81a projecting outward in a width direction of the operating plate 81 is arranged on the pair of rail portions 33 of the housing 30 in the initial state. Because the operating plate 81 is sufficiently thin, this has flexibility with which this may be bent in a direction orthogonal to a surface direction of the operating plate 81, that is, in a direction away from the inner needle 14 (refer to FIG. 9B). A material forming the operating plate 81 (catheter operating member 80) is not especially limited, and for example, the material cited with the catheter hub 20 may be appropriately selected.

Figure 8A:
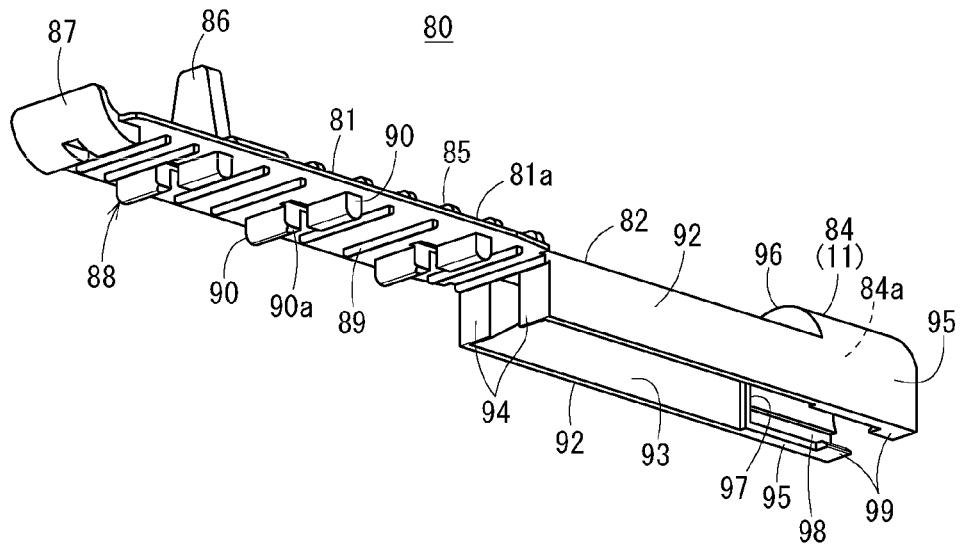
FIG. 8A is a perspective view of a catheter operating member in FIG. 1 as seen from below.
Figure 8B:
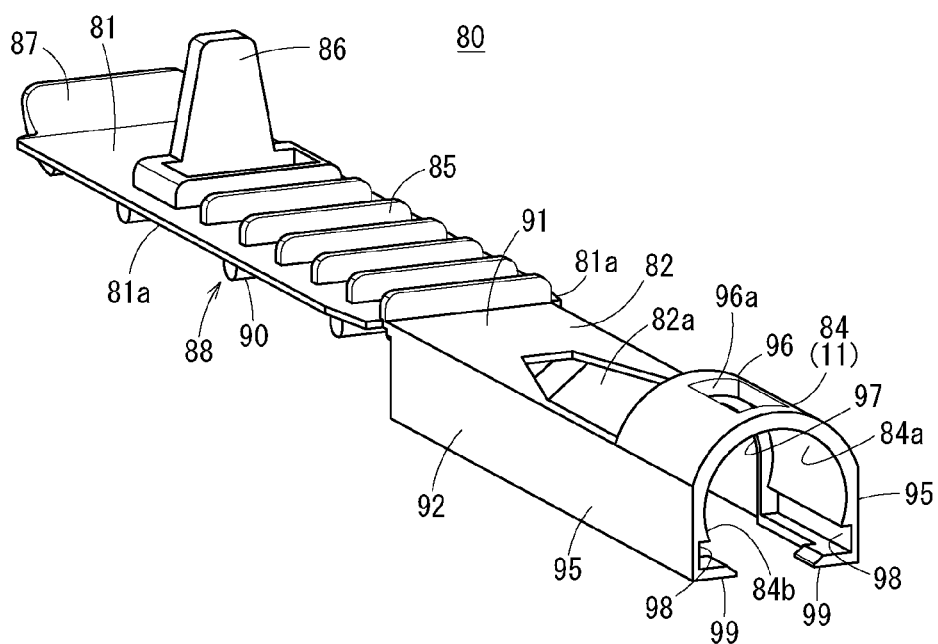
FIG. 8B is a perspective view of the catheter operating member as seen from a proximal end side.

As illustrated in FIGS. 1, 8A, and 8B, an upper rib 85 and a tab 86 are provided on an upper surface of the operating plate 81, a distal end warped portion 87 is provided on a distal end of the operating plate 81, and a holding unit 88 and a lower rib 89 are provided on a lower surface of the operating plate 81.

One or more (three in FIG. 8A) holding units 88 of the catheter operating member 80 are provided in a longitudinal direction of the operating plate 81 and are brought into contact with an outer peripheral surface of the catheter 12 at each portion to hold the same. Each holding unit 88 is formed of a pair of projections 90 projecting downward from the lower surface of the operating plate 81. The pair of projections 90 is symmetrical to each other across an intermediate portion in the width direction of the operating plate 81 and is formed into a wide rectangular shape. The catheter 12 is held by being caught by clicks 90a of the pair of projections 90 to be held between the pair of projections 90 at the time of assembly with the catheter operating member 80.

The hub arranging unit 82 of the catheter operating member 80 is formed to be longer than the catheter hub 20 in an axial direction and accommodates the catheter hub 20 therein. The hub arranging unit 82 includes an upper plate 91 continued from the operating plate 81 at the same height and a pair of side plates 92 coupled to a lower surface of the upper plate 91 and extending in the proximal end direction. A lower side of the hub arranging unit 82 is an opening portion 93 in which a space of the hub arranging unit 82 is opened.

The upper plate 91 is formed to be slightly narrower than the pair of side edges 81a of the operating plate 81. The upper plate 91 partially covers only a distal end side (small-diameter portion 23) of the catheter hub 20, thereby forming an exposing portion 82a to expose a proximal end side (the transition portion 22 and the large-diameter portion 21) of the catheter hub 20 on a side closer to the proximal end than the upper plate 91. A distal end side of the exposing portion 82a is formed into a substantially triangular shape that becomes gradually narrower toward the distal end. As a result, in the initial state, a distal end side of the small-diameter portion 23 of the catheter hub 20 and the upper plate 91 are sufficiently brought close to each other, and the catheter 12 may be held in a satisfactory condition by the operating plate 81.

A pair of side plates 92 is continuous to both side edges of the upper plate 91 and extends in parallel from a boundary between the operating plate 81 and the upper plate 91 in the proximal end direction. The pair of side plates 92 is accommodated inside the pair of side walls 32 of the housing 30 and is spaced apart with a width with which this may be out of contact with the flange 24 of the catheter hub 20. A triangular coupling block 94 having a distal end face at right angle with the upper plate 91 and a proximal end face inclined is formed on the lower surface of the upper plate 91 and inside a distal end of the pair of side plates 92. The upper plate 91 and the pair of side plates 92 are firmly connected by the coupling block 94.

The connecting unit 84 is coupled to the proximal ends of the pair of side plates 92 and covers an upper portion and both side portions of the outer tube 71 (accommodating body 72) of the safety mechanism 60. In detail, this includes a pair of proximal end side plates 95 connected to the pair of side plates 92 and a proximal end semi-tubular portion 96 continuous to an upper portions of the pair of proximal end side plates 95 to bridge by forming an arc shape, and a mounting chamber 84a is formed therein. A proximal end of the connecting unit 84 serves as a proximal end communication opening 84b that opens the mounting chamber 84a. Also, at the boundary between the hub arranging unit 82 and the connecting unit 84 (a distal end of the pair of proximal end side plates 95 and the proximal end semi-tubular portion 96), an operating projection 97 projecting radially inward to be able to transmit operating force to the catheter hub 20 and the safety mechanism 60 is provided.

An outer surface side of each proximal end side plate 95 is a flat surface along the pair of side walls 32 of the housing 30. On the other hand, an inner surface side of each proximal end side plate 95 forming the mounting chamber 84a is an arc surface conforming to an outer diameter of the cylindrical accommodating body 72. Also, on the inner surfaces of the proximal end side plates 95, a pair of concave strips 98 extending from the operating projection 97 in the proximal end direction and communicated with the proximal end communication opening 84b is formed. In the initial state, the pair of concave strips 98 slidably accommodates the pair of projected strips 75 of the accommodating body 72.

Holding convex portions 99 projecting inward in a width direction are provided on the proximal end side of the pair of proximal end side plates 95 on a side lower than the concave strips 98. A pair of holding convex portions 99 inhibits the outer tube 71 from falling from the opening portion on the lower side of the connecting unit 84.

The inner surface of the proximal end semi-tubular portion 96 is an arc surface smoothly continuing to the inner surface of each proximal end side plate 95 and conforming to the outer shape of the accommodating body 72. Thus, the connecting unit 84 allows the accommodating body 72 to be separated only from the proximal end communication opening 84b. In addition, a rectangular long window 96a elongated in the axial direction is provided on an upper portion of the proximal end semi-tubular portion 96. The long window 96a allows expansion of the upper arm 63 when the pair of arms 63 of the inner tube 61 is exposed from the accommodating body 72.

As illustrated in FIGS. 3, 8A, and 8B, the operating projection 97 of the catheter operating member 80 extends in a circumferential direction on the inner peripheral surfaces of the pair of proximal end side plates 95 and the proximal end semi-tubular portion 96. In the initial state, the operating projection 97 is arranged between the outer annular convex portion 58 of the valve mechanism 50 and the distal end of the outer tube 71 (accommodating body 72), and faces the proximal end face of the outer annular convex portion 58 and the distal end face of the outer tube 71 in a range of half circumference or more in the circumferential direction. Therefore, when the user applies advancing operating force for advancing the catheter operating member 80, the operating projection 97 comes into contact with the outer annular convex portion 58, and the advancing operating force is smoothly transmitted to the outer annular convex portion 58. Conversely, when the user performs a retraction operating force to retract the catheter operating member 80, the operating projection 97 comes into contact with the outer tube 71, and the retracting operating force is smoothly transmitted to the outer tube 71.

In the catheter assembly 10 configured as described above, the inner needle 14 fixed to the housing 30 is inserted in the catheter 12 to form a double-layered needle and the needle tip 15 projects from the distal end of the catheter 12 in the initial state (puncturable state) illustrated in FIG. 1. In addition, the operating plate 81 of the catheter operating member 80 holds the double-layered needle with appropriate holding force by holding the catheter 12 with the holding unit 88. The operating plate 81 is arranged on the rail portion 33 of the housing 30, so that linearity thereof is maintained. Furthermore, at the distal end of the housing 30, the supporting member 45 stands by so as to be able to support a lower side of the double-layered needle.

As illustrated in FIGS. 3 and 9A, the outer tube 71 of the safety mechanism 60 is accommodated in the connecting unit 84 of the catheter operating member 80. In this accommodated state, relative movement of the connecting unit 84 in a vertical direction or a width direction with respect to the safety mechanism 60 is restricted. The inner tube 61 is accommodated in the outer tube 71 so as to freely advance and retract, and the pair of arms 63 interposes and hold the connector 55 of the valve mechanism 50. Furthermore, the valve main body 51 of the valve mechanism 50 is inserted to be fitted in the catheter hub 20.

That is, the valve mechanism 50 of the first assembly 16, the safety mechanism 60 of the second assembly 18, and the connecting unit 84 of the catheter operating member 80 form the separation restricting mechanism 11 to restrict the separation in an inserted state in which the inner needle 14 is inserted in the catheter 12. By the separation restricting mechanism 11, when the inserted state continues, even if the first assembly 16 is exposed from the housing 30, this is continuously connected with the catheter operating member 80 with strong connecting strength, and advances and retracts together with the catheter operating member 80.

Basically, the catheter assembly 10 according to the first embodiment is configured as described above, and a function effect thereof is described below.

When forming the introducing unit of the infusion into the patient, the user uses the catheter assembly 10 illustrated in FIG. 9A and grasps to operate the housing 30 to puncture the patient with the double-layered needle (puncture operation). At the time of puncture, the holding unit 88 holds the catheter 12 and the supporting member 45 supports the catheter 12 from below, so that bending of the double-layered needle is inhibited.

Then, in a punctured state of the double-layered needle, the user relatively advances the first assembly 16 with respect to the inner needle 14 and the housing 30, and inserts the catheter 12 in the blood vessel (catheter advancement operation). At that time, the user puts his/her finger on the upper rib 85 or the tab 86 of the catheter operating member 80 and slides the catheter operating member 80 in the distal end direction. The operating plate 81 of the catheter operating member 80 is such that the distal end warped portion 87 comes into contact with the skin and the like of the patient to be bent away from the double-layered needle together with the advance in the distal end direction. As a result, each holding unit 88 sequentially removes the held catheter 12.

The side plate 92 and the coupling block 94 of the catheter operating member 80 are brought into contact with the supporting member 45 when getting out of the housing 30, thereby rotating the supporting member 45 to the outside of the housing 30. As a result, the catheter operating member 80 and the safety mechanism 60 get out of the distal end of the housing 30 and are exposed to the outside.

As illustrated in FIG. 9B, at the time of the catheter advancement operation, the operating projection 97 of the catheter operating member 80 is brought into contact with the outer annular convex portion 58 of the valve mechanism 50 and presses the same in the distal end direction. That is, the advancing operating force of the user is transmitted to the first assembly 16 to integrally advance the first assembly 16 and the safety mechanism 60. On the other hand, when the user retracts the catheter operating member 80, as illustrated in FIG. 9C, the operating projection 97 comes into contact with the distal end face of the outer tube 71 and presses the same in the proximal end direction. By this, the retracting operating force of the user is transmitted to the safety mechanism 60 to integrally retract the first assembly 16 and the safety mechanism 60.

After the catheter 12 is sufficiently advanced into the blood vessel by the catheter advancement operation, the housing 30 is withdrawn in the proximal end direction to remove the inner needle 14 from the patient while the catheter 12 is remained inserted (inner needle retraction operation). At that time, the user retracts the inner needle 14 and the housing 30 relative to the first assembly 16, the safety mechanism 60, and the catheter operating member 80 so as to separate them from the first assembly 16.

Figure 4:
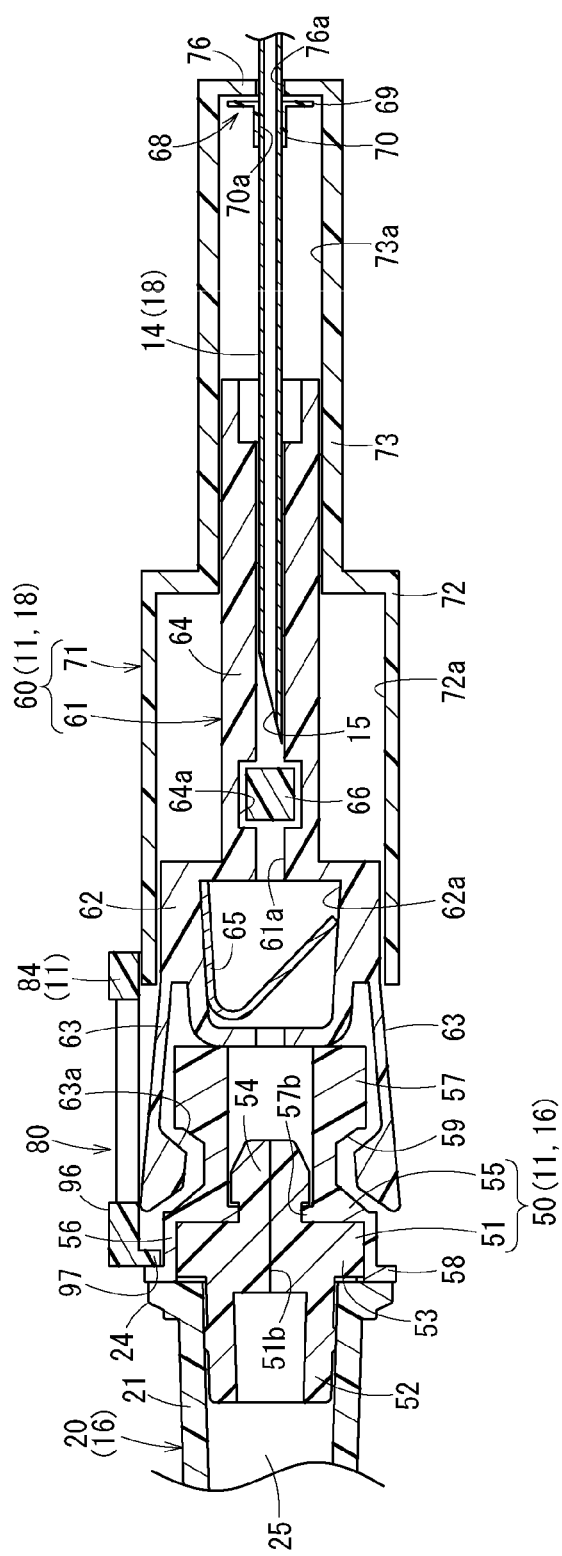
FIG. 4 is a side sectional view illustrating the separation restricting mechanism in a non-inserted state of the catheter assembly in FIG. 1.

In the safety mechanism 60, because the inner needle 14 retracts toward the proximal end than the shutter 65 in the inner tube 61 at the time of the inner needle retraction operation, the shutter 65 pushed in by the inner needle 14 develops in front of the needle tip 15 to inhibit the re-exposure of the needle tip 15 (refer also to FIG. 4). Also, as the inner needle 14 retracts toward the proximal end than the stopper 66, the stopper 66 is put into a free state, and relative movement between the inner tube 61 and the outer tube 71 becomes possible (refer also to FIG. 6B). Furthermore, when the inner needle 14 retracts, the vicinity of the needle tip 15 is caught by the retaining member 68. As a result, the needle tip 15 is accommodated in the safety mechanism 60 in an unremovable condition.

At the time of the inner needle retraction operation, the outer tube 71 is pulled by the inner needle 14 caught by the retaining member 68. Therefore, as illustrated in FIG. 10A, the outer tube 71 relatively retracts in the proximal end direction with respect to the first assembly 16 and the catheter operating member 80. When the outer tube 71 retracts, the inner tube 61 relatively advances with respect to the outer tube 71 by the valve mechanism 50 of which movement is restricted by the catheter operating member 80, and is delivered from the distal end of the outer tube 71. As a result, the pair of arms 63 is opened, and the connection of the valve mechanism 50 by the pair of hooks 63a may be released (refer also to FIG. 4).

Also, the catheter operating member 80 relatively advances with respect to the outer tube 71 because the operating projection 97 is interposed between the pair of arms 63 and the valve mechanism 50. As a result, the outer tube 71 moves in the mounting chamber 84a of the connecting unit 84 in the proximal end direction to separate from the proximal end communication opening 84b. At that time, the pair of concave strips 98 of the catheter operating member 80 guides the pair of projected strips 75 of the outer tube 71 to slide.

Herein, the first assembly 16 is not held by the catheter operating member 80; only the valve mechanism 50 is connected to the inner tube 61. Therefore, as illustrated in FIG. 10B, the first assembly 16 is also movable from the catheter operating member 80 in accordance with the disconnection of the valve mechanism 50 due to the expansion of the pair of hooks 63*a*.

Therefore, as illustrated in FIG. 10C, the first assembly 16 exits the opening portion 93 of the catheter operating member 80 (hub arranging unit 82). On the other hand, the catheter operating member 80 is also separated from the safety mechanism 60 (second assembly 18) that exits the connecting unit 84 together with the separation of the first assembly 16.

That is, in a non-inserted state in which the inner needle 14 separates from the catheter 12 by the inner needle retraction operation, the separation restricting mechanism 11 has weak connecting strength to allow separation of the first assembly 16, the safety mechanism 60, and the catheter operating member 80 from one another. As a result, the first assembly 16 may be indwelled in the patient in a satisfactory condition. On the other hand, the second assembly 18 and the catheter operating member 80 separated from the first assembly 16 are easily discarded by the user. Note that, in the first embodiment, the connecting strength becomes zero in the non-inserted state, but the first assembly 16 may also be connected to the second assembly 18 and the catheter operating member 80 with connecting strength greater than zero such as frictional force.

As described above, the catheter assembly 10 may restrict separation of the first assembly 16 and the catheter operating member 80 in the inserted state by the separation restricting mechanism 11 provided separately from the housing 30. Therefore, even when the first assembly 16 is exposed from the housing 30, the connection between the first assembly 16 and the catheter operating member 80 continues, and the operating force of the catheter operating member 80 is surely transmitted to the first assembly 16. On the other hand, the separation restricting mechanism 11 allows separation of the first assembly 16 from the catheter operating member 80 in the non-inserted state in which the inner needle 14 is separated from the catheter 12. As a result, the catheter operating member 80 and the first assembly 16 may be smoothly separated from each other without large force, and the first assembly 16 may be indwelled on the patient side.

Especially, the catheter assembly 10 may restrict the separation of the first assembly 16, the second assembly 18, and the catheter operating member 80 from each other by restricting the separation of the second assembly 18 from the catheter operating member 80 in the inserted state. In contrast, it is possible to smoothly separate the first assembly 16, the second assembly 18, and the catheter operating member 80 from each other by allowing the separation of the second assembly 18 from the catheter operating member 80 in the non-inserted state. Also, the relative movement of the catheter operating member 80 in a direction other than the axial direction of the inner needle 14 is restricted by the connecting unit 84, so that it is possible to easily relatively move the first assembly 16 along the axial center of the inner needle 14.

Furthermore, the catheter assembly 10 is provided with the safety mechanism 60 on a side closer to the proximal end than the first assembly 16, and the separation of the safety mechanism 60 from the connecting unit 84 is restricted in the inserted state. As a result, even in a position where the safety mechanism 60 is separated from the housing 30, the connection between the catheter operating member 80 and the second assembly 18 is satisfactory continued. In addition, because the catheter operating member 80 includes the operating projection 97, in the advancement operation of the catheter operating member 80, the operating projection 97 is pressed against the first assembly 16 and the operating force may be surely transmitted to the first assembly 16. In contrast, in the retraction operation of the catheter operating member 80, the operating projection 97 is pressed against the safety mechanism 60, and the operating force may be surely transmitted to the operating projection 97. Furthermore, by allowing the separation of the first assembly 16 from the catheter operating member 80 at a stage when an exposure of the needle tip 15 is inhibited, safety at the time of user handling is improved. an Note that the catheter assembly 10 is not limited to the above-described configuration, and various variations and applications may also be adopted. For example, it is possible to configure such that the catheter operating member 80 is not provided with the valve mechanism 50 and the pair of arms 63 of the inner tube 61 holds the catheter hub 20. In this case, the connecting unit 84 of the catheter operating member 80 may be brought into contact with the proximal end of the catheter hub 20 to transmit the advancing operating force at the time of the advancement operation. Also, the catheter assembly 10 may be provided with a guide wire that is inserted in the inner needle 14 and may advance and retract with respect to the inner needle 14.

Hereinafter, the variation of the catheter assembly 10 and other embodiments (second to fifth embodiments) are described. Note that, in the following description, the same reference numeral is assigned to the same component or a component having the same function as that of the catheter assembly 10 according to the first embodiment, and the detailed description thereof is omitted.

Figure 11:
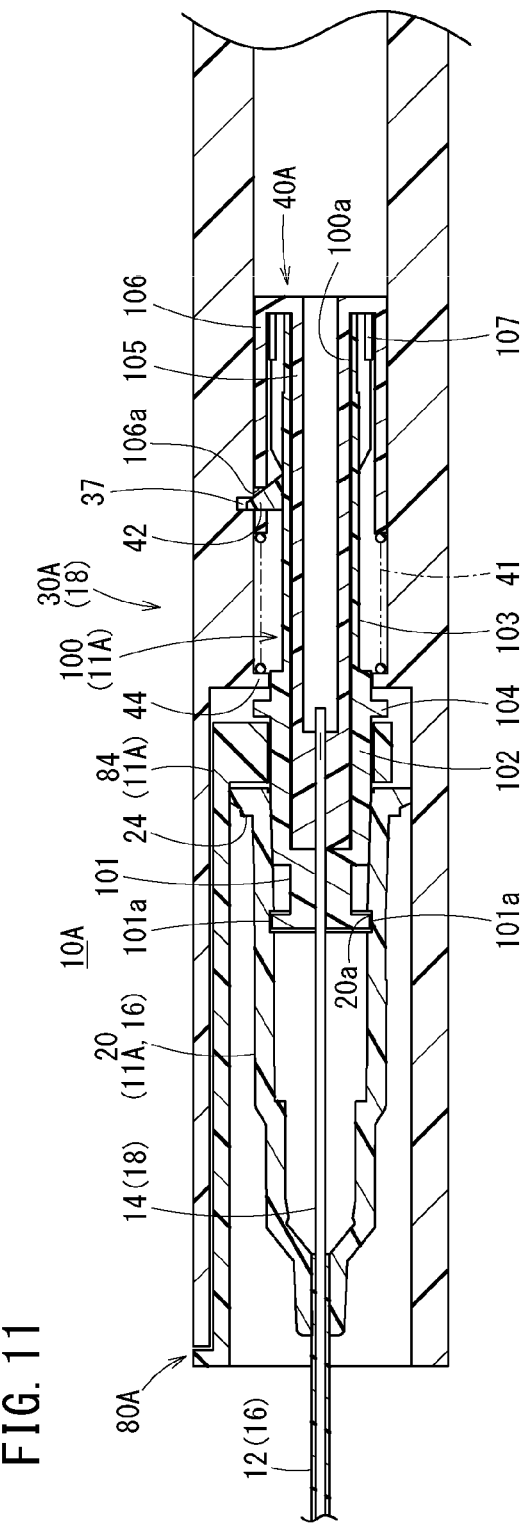
FIG. 11 is a side sectional view partially illustrating a catheter assembly according to a first variation.

A catheter assembly 10A according to a first variation illustrated in FIG. 11 different from the catheter assembly 10 according to the first embodiment in that this is provided with a blood scattering prevention cover 100 as an auxiliary member for accommodating an inner needle 14 and has a structure of automatically retracting the inner needle 14. A separation restricting mechanism 11A is formed of a catheter hub 20, a connecting unit 84 of a catheter operating member 80A, and the blood scattering prevention cover 100.

Although the structure of automatically retracting the inner needle 14 is not especially limited, for example, it may be configured to retract a needle holding member 40A that holds the inner needle 14 by energization of an elastic member (coil spring 41 or the like) by a fact that the catheter hub 20 is separated from a housing 30A at a predetermined distance as a trigger. Specifically, the housing 30A is formed into a bottomed square tube shape with a distal end opened. In the housing 30A, the blood scattering prevention cover 100, a tubular needle holding member 40A accommodated in the blood scattering prevention cover 100, and a coil spring 41 for energizing the needle holding member 40A in a proximal end direction are provided in an initial state. In the initial state, the needle holding member 40A is engaged with the housing 30A by a lock member 42, and movement thereof in the proximal end direction is restricted.

The blood scattering prevention cover 100 includes a head piece 101 for removably coupling a catheter hub 20 in the catheter hub 20, a distal end body portion 102 extending from the head piece 101 in the proximal end direction on which the catheter operating member 80A is externally mounted, and a proximal end body portion 103 extending from the distal end body portion 102 in the proximal end direction by a predetermined length. An accommodation hole 100*a* in which the needle holding member 40A is accommodated is provided inside the distal end body portion 102 and the proximal end body portion 103.

A pair of head pieces 101 of the blood scattering prevention cover 100 is provided so as to interpose the inner needle 14, and on an outer peripheral surface thereof, a catch portion 101a inserted in a coupling groove 20a provided on an inner surface of the catheter hub 20 is formed so as to project radially outward. In the initial state, the pair of head pieces 101 is such that the inner needle 14 is arranged between them and distal ends thereof are separated in opposite directions to engage the catch portion 101a with the coupling groove 20a. On the other hand, when the inner needle 14 is no longer arranged between them, the distal ends are brought close to each other, thereby disengaging the catch portion 101a from the coupling groove 20a.

The distal end body portion 102 is formed into a cylindrical shape and is fitted to the inner surface of the catheter hub 20 to seal a hollow portion 25. The catheter operating member 80A is provided with a connecting unit 84 in a C shape in a cross-sectional view orthogonal to a longitudinal direction on a proximal end thereof, and a C-shaped inner space is opened downward. The connecting unit 84 is slidably arranged outside the distal end body portion 102 of the blood scattering prevention cover 100 exposed from a proximal end of the catheter hub 20. Also, on an outer peripheral surface of the distal end body portion 102, a projection 104 facing a proximal end of the connecting unit 84 is projected.

On the other hand, the proximal end body portion 103 has a cylindrical shape than that of the distal end body portion 102 and is inserted to a side closer to the proximal end than a seat (annular projection 44) of a coil spring 41 in the housing 30A in the initial state. The lock member 42 is arranged in an intermediate position of an outer peripheral surface of the proximal end body portion 103. A guide projection 107 is provided on a proximal end side of the proximal end body portion 103 for guiding the lock member 42 and restricting the separation of the blood scattering prevention cover 100 from the housing 30A.

The needle holding member 40A includes an inner holding unit 105 inserted in the blood scattering prevention cover 100 to hold the inner needle 14 on a distal end thereof and an outer receiving tube 106 projecting radially outward from a proximal end of the inner holding unit 105 and further extending in a distal end direction out of the inner holding unit 105. In a predetermined position of the outer receiving tube 106, a through hole 106a through which the lock member 42 is arranged to penetrate is provided. A distal end face of the outer receiving tube 106 is configured as the seat that receives the coil spring 41.

The lock member 42 is formed into a triangular shape in a side sectional view and penetrates the through hole 106a of the needle holding member 40A in a state of being arranged on an outer peripheral surface of the blood scattering prevention cover 100, and a part thereof is inserted in a locking hole 37 provided on an inner surface of the housing 30A. As a result, the lock member 42 makes the blood scattering prevention cover 100 relatively slidable while restricting the movement of the needle holding member 40A in the proximal end direction in the initial state.

Figure 12:
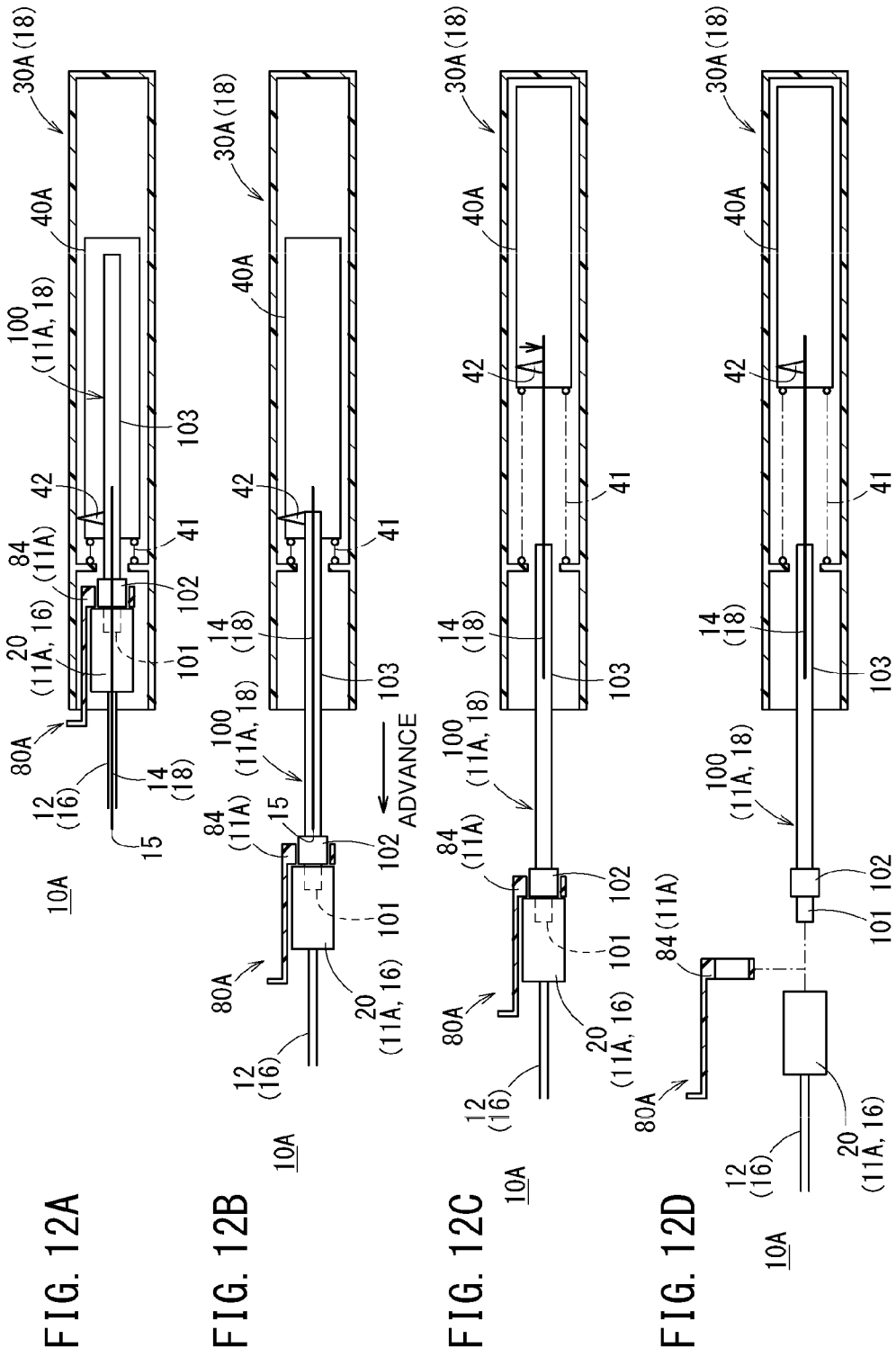
FIG. 12A is a first illustrative view schematically illustrating operation of the catheter assembly in FIG. 11.
FIG. 12B is a second illustrative view of operation following FIG. 12A.
FIG. 12C is a third illustrative view of operation following FIG. 12B.
FIG. 12D is a fourth illustrative view of operation following FIG. 12C.

Basically, the catheter assembly 10A according to the first variation is configured as described above, and a function effect thereof is hereinafter described. As illustrated in FIGS. 11 and 12A, the catheter assembly 10A restricts separation of the catheter hub 20, the connecting unit 84 of the catheter operating member 80, and the blood scattering prevention cover 100 in an inserted state that the inner needle 14 is inserted in the catheter 12. In this state, as in the first embodiment, puncture operation and catheter advancement operation are performed.

In the catheter advancement operation, as a user pushes out the catheter operating member 80A, as illustrated in FIG. 12B, the connecting unit 84 of the catheter operating member 80A comes into contact with the proximal end of the catheter hub 20 to advance a first assembly 16. At that time, while the blood scattering prevention cover 100 connected to the first assembly 16 advances, the needle holding member 40A continues a state in which the movement is restricted by the lock member 42. When the user retracts the catheter operating member 80A, the connecting unit 84 comes into contact with a projection 104 (refer to FIG. 11) of the blood scattering prevention cover 100 to retract the blood scattering prevention cover 100.

When the catheter 12 is inserted in a patient by the catheter advancement operation, the user performs an inner needle retraction operation of retracting the inner needle 14 and the housing 30A. In the inner needle retraction operation, as the housing 30A and the needle holding member 40A retract in the proximal end direction, the blood scattering prevention cover 100 relatively moves to the distal end side. As a result, the needle tip 15 of the inner needle 14 is accommodated in the blood scattering prevention cover 100, and scattering of blood attached to the inner needle 14 is prevented.

Thereafter, as illustrated in FIG. 12C, when the lock member 42 moves toward the proximal end than the blood scattering prevention cover 100, the lock member 42 exits the locking hole 37 of the housing 30A. Then, the needle holding member 40A energized in the proximal end direction by the coil spring 41 retracts in the proximal end direction as the coil spring 41 elastically expands on the basis of unlocking of the lock member 42. As a result, the inner needle 14 automatically retracts to be accommodated in the housing 30A, and re-exposure of the needle tip 15 is prevented.

When the blood scattering prevention cover 100 advances to a certain extent from the housing 30A, the guide projection 107 is caught by the annular projection 44 in the housing 30A, so that the blood scattering prevention cover 100 is inhibited from dropping from the housing 30A. At a stage at which the inner needle 14 exits the catheter hub 20 (in a non-inserted state in which the inner needle 14 is separated from the catheter 12), the head piece 101 of the blood scattering prevention cover 100 is bent inward and the coupling with the catheter hub 20 is released. Along with this, the catheter operating member 80A may advance relative to the blood scattering prevention cover 100. Therefore, as illustrated in FIG. 12D, the first assembly 16 and the second assembly 18 (the blood scattering prevention cover 100) are separated by the catheter operating member 80A pushing out the first assembly 16, and the catheter operating member 80A is separated from the first and second assemblies 16 and 18.

As described above, the catheter assembly 10A according to the first variation may also obtain the effect similar to that of the catheter assembly 10. Especially, the second assembly 18 of the catheter assembly 10A may further improve safety at the time of handling (disposal) by automatically retracting the inner needle 14 and accommodating in the housing 30A.

Second Embodiment

As illustrated in FIGS. 13 to 18C, a catheter assembly 110 according to a second embodiment is different from catheter assemblies 10 and 10A in a structure of a safety mechanism 160 (auxiliary member) and a structure of a catheter operating member 180 corresponding to the same. Note that a configuration of a first assembly 116 is basically similar to that of the first embodiment, but a connector 55 of a valve mechanism 50 is not provided with an outer annular convex portion 58. A separation restricting mechanism 111 is formed of the valve mechanism 50 of the first assembly 116, the safety mechanism 160 of a second assembly 118, and a connecting unit 184 of the catheter operating member 180.

As illustrated in FIGS. 14 to 16B, the safety mechanism 160 includes an accommodating main body 161 for accommodating a needle tip 15 of an inner needle 14 and a movable member 170 provided separately from the accommodating main body 161 and movable relative to the same. An insertion hole 161a of the inner needle 14 is provided inside the accommodating main body 161 and a member space 161b for accommodating and fixing a retaining member 68 of the inner needle 14 is formed on a proximal end side of the insertion hole 161a. Note that the movable member 170 may be coupled to (integrally molded with) the accommodating main body 161 with a coupling arm or the like not illustrated.

The accommodating main body 161 includes a cylindrical portion 162 detachably attached to the connecting unit 184 of the catheter operating member 180 and a head portion 163 projecting from a central portion of a distal end face of the cylindrical portion 162 in a distal end direction. On an outer peripheral surface of the cylindrical portion 162, a pair of projected strips 164 projecting in directions opposite to each other outward in a width direction and linearly extending in an axial direction of the cylindrical portion 162 is provided. A cutout space 165 reaching an axial center of the cylindrical portion 162 is formed on the outer peripheral surface on an upper side of the cylindrical portion 162 in an initial state.

The cutout space 165 includes a rectangular parallelepiped-shape deep space 165a provided in the vicinity of the axial center of the cylindrical portion 162 and a shallow space 165b continuous from an upper portion of the deep space 165a and having a shape larger in axial and width directions than that of the deep space 165a and is formed into a stepped space. The movable member 170 is accommodated in the cutout space 165 so as to be freely displaced.

The deep space 165a is provided so as to divide the insertion hole 161a extending in the axial direction near the distal end of the cylindrical portion 162, thereby being communicated with the insertion hole 161a on both front and rear sides. In contrast, a plurality of locking pieces 166 is formed so as to project on an inner surface on a distal end side and an inner surface on a proximal end side of the cylindrical portion 162 forming the shallow space 165b. Two locking pieces 166 on the inner surface on the distal end side are inclined diagonally downward in a proximal end direction and two locking pieces 166 on the inner surface on the proximal end side are inclined diagonally downward in a distal end direction. A plurality of locking pieces 166 is provided at the same horizontal height within the cylindrical portion 162, and when the movable member 170 is displaced downward to get over each locking piece 166, they cooperate with each other to lock the movable member 170.

Also, the head portion 163 of the accommodating main body 161 is formed into a cylindrical shape so as to be able to fit to a proximal end accommodating unit 57a of the valve mechanism 50 (connector 55). In the initial state, the head portion 163 is inserted in the proximal end accommodating unit 57a, so that the connector 55 of the valve mechanism 50 is in close contact with the distal end face of the cylindrical portion 162.

In contrast, the movable member 170 is formed as a member having a cross shape as seen in a front view with plate-shaped vertical plate 171 and horizontal plate 172 intersecting at 90 degrees. The vertical plate 171 extends in a vertical direction to be arranged in the deep space 165a and the shallow space 165b. A portion above a coupling site to the horizontal plate 172 of a proximal end face of the vertical plate 171 is formed to be a tapered surface 171a. Furthermore, a needle tip accommodating hole 171b tapered to be closed is provided in a position below the coupling site to the horizontal plate 172 of the proximal end face of the vertical plate 171. In contrast, the horizontal plate 172 is arranged in the shallow space 165b so as to extend in the width direction and the axial direction of the cylindrical portion 162.

Figure 14:
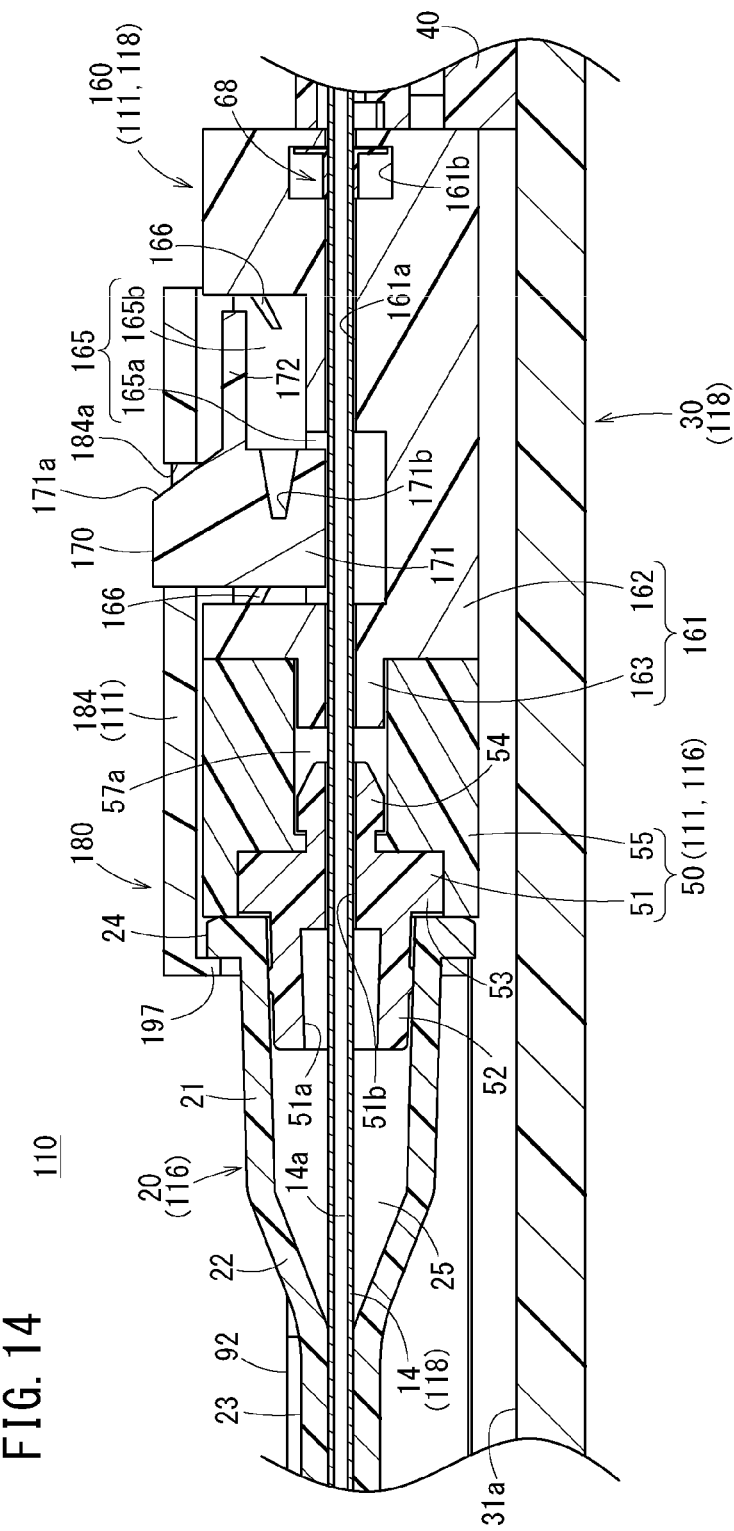
FIG. 14 is a side sectional view illustrating a separation restricting mechanism in an inserted state of the catheter assembly in FIG. 13.
Figure 15:
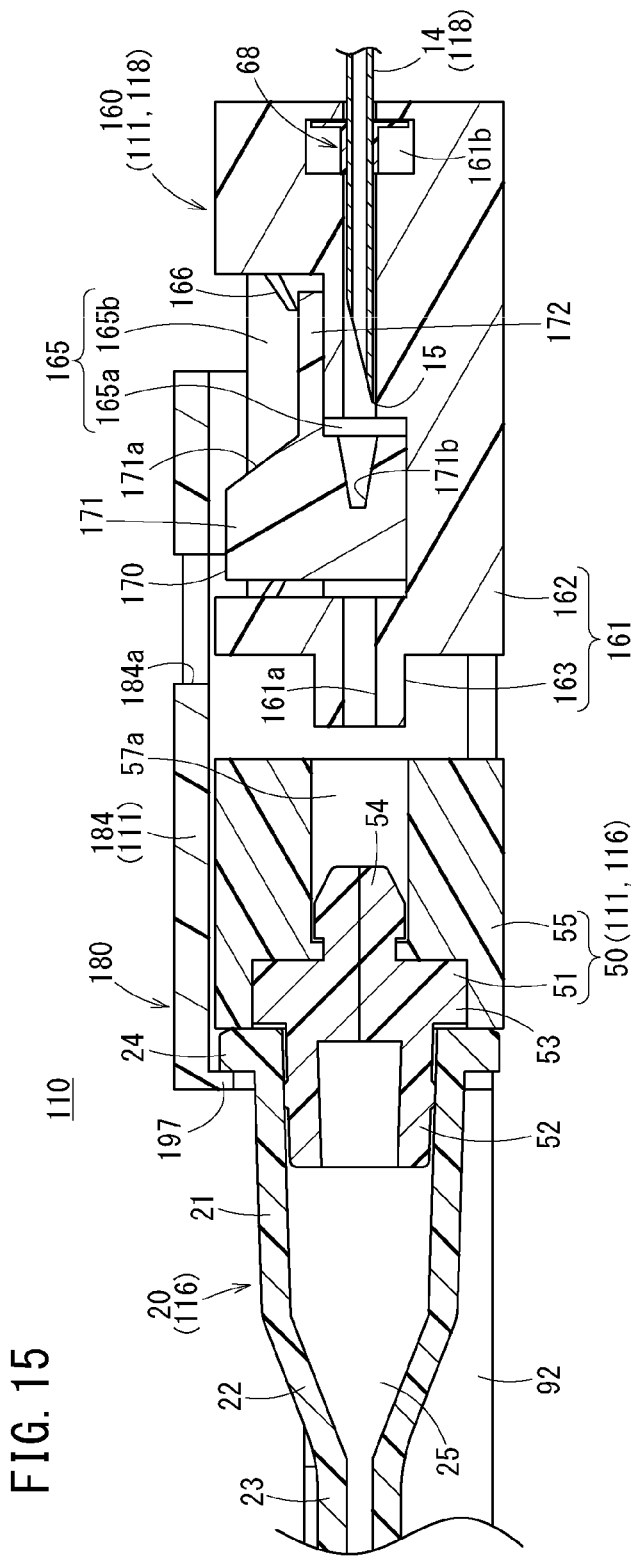
FIG. 15 is a side sectional view illustrating the separation restricting mechanism in a non-inserted state of the catheter assembly in FIG. 13.
Figure 16A:
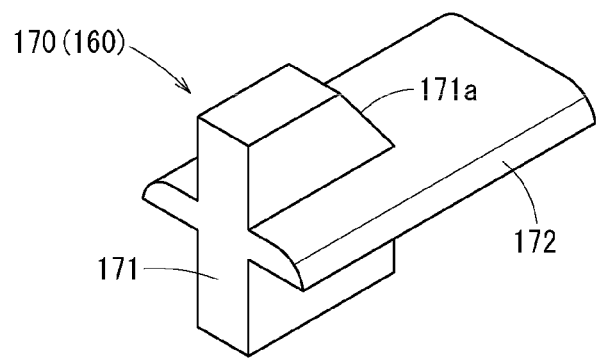
FIG. 16A is a perspective view illustrating a movable member of a safety mechanism in FIG. 13.
Figure 16B:
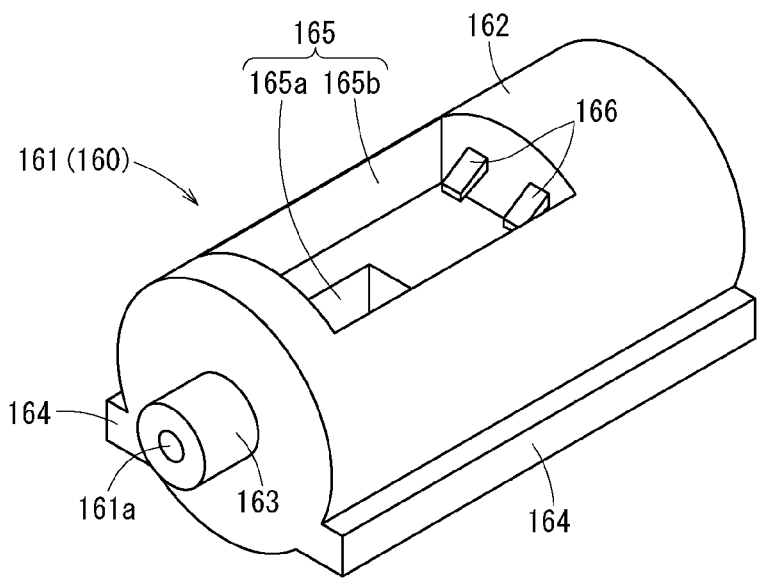
FIG. 16B is a perspective view illustrating an accommodating main body of the safety mechanism in FIG. 13.

As illustrated in FIG. 14, the movable member 170 configured as described above is arranged on an upper side of the cutout space 165 and displacement downward is restricted because the inner needle 14 penetrates the deep space 165a in the initial state. Therefore, the vertical plate 171 of the movable member 170 plays a role as a lock function of locking the catheter operating member 180. On the other hand, as illustrated in FIG. 15, when the inner needle 14 retracts from the deep space 165a, the movable member 170 may be displaced to a lower side of the cutout space 165. Then, this is displaced downward as the catheter operating member 180 advances, allows the needle tip accommodating hole 171b to face the insertion hole 61a, and a plurality of locking pieces 166 of the cylindrical portion 162 and the horizontal plate 172 are locked.

Figure 13:
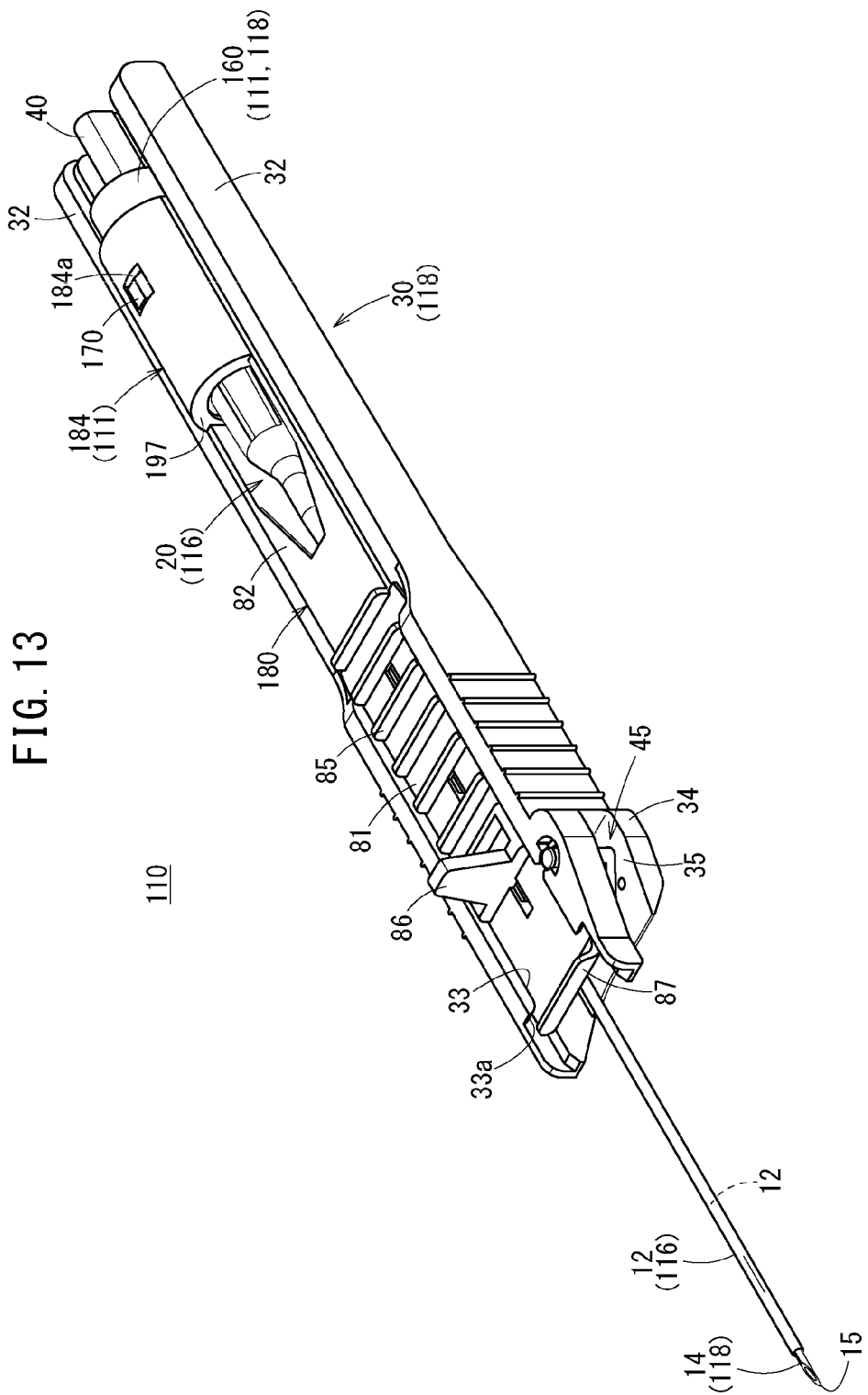
FIG. 13 is a perspective view illustrating a catheter assembly according to a second embodiment of the present invention.

Also, as illustrated in FIGS. 13 to 15, the connecting unit 184 of the catheter operating member 180 is formed to be longer in the axial direction than the connecting unit 84 of the first embodiment. An operating projection 197 having a shape similar to that of the first embodiment is provided at a distal end of the connecting unit 184 (boundary position of a hub arranging unit 82); in the initial state, the operating projection 197 is located on a side closer to a distal end than a flange 24 of a catheter hub 20.

A rectangular insertion opening 184a in which the vertical plate 171 of the movable member 170 is inserted is provided on an upper portion and in a central portion in the width direction of the connecting unit 184. The insertion opening 184a is formed so as to have dimensions in axial and width directions smaller than those of the horizontal plate 172 of the movable member 170, inhibiting the movable member 170 from getting out of the insertion opening 184a. In the initial state, the movable member 170 is located on the upper side of the cutout space 165 as described above, so that the vertical plate 171 is continuously arranged in the insertion opening 184a. Therefore, advancing operating force of the catheter operating member 180 by a user is transmitted from an opening edge of the insertion opening 184a to the movable member 170 (vertical plate 171) to advance and retract the safety mechanism 160. Because the safety mechanism 160 is connected to the first assembly 116, the operating force of the catheter operating member 180 is eventually transmitted also to the first assembly 116.

The catheter assembly 110 according to the second embodiment is basically configured as described above, and a function effect thereof is hereinafter described. As illustrated in FIG. 17A, the separation restricting mechanism 111 of the catheter assembly 110 restricts separation of the valve mechanism 50, the safety mechanism 160, and the connecting unit 184 of the catheter operating member 180 in an inserted state in which the inner needle 14 is inserted in the catheter 12. In this state, as in the first embodiment, a puncture operation and a catheter advancement operation are performed.

As illustrated in FIG. 17B, in the catheter advancement operation, as the user pushes out the catheter operating member 180, the opening edge of the insertion opening 184a is brought into contact with the movable member 170 and pushes out the safety mechanism 160. As a result, the safety mechanism 160 advances and the first assembly 116 connected to the safety mechanism 160 also advances. Also, as illustrated in FIG. 17C, when the user retracts the catheter operating member 180, the opening edge of the insertion opening 184a pushes the movable member 170 in the proximal end direction and the operating projection 197 pushes the flange 24 of the catheter 12 in the proximal end direction, so that the first assembly 116 and the safety mechanism 160 are retracted.

When the catheter 12 is inserted in a patient by the catheter advancement operation, the user performs an inner needle retraction operation of retracting the inner needle 14 and a housing 30. As illustrated in FIG. 18A, in the inner needle retraction operation, the needle tip 15 moves toward the proximal end than the movable member 170, so that the movable member 170 may be displaced downward. That is, the safety mechanism 160 and the catheter operating member 180 are unlocked, and as illustrated in FIG. 18B, the catheter operating member 180 may advance relative to the safety mechanism 160.

Also, the catheter hub 20 of which movement in the distal end direction is restricted by the operating projection 197 of the catheter operating member 180 may also advance relative to the safety mechanism 160. As a result, as illustrated in FIG. 18C, the first assembly 116 (valve mechanism 50), the second assembly 118 (safety mechanism 160), and the catheter operating member 180 are separated from one another.

In contrast, as the catheter operating member 180 advances, the movable member 170 is such that the tapered surface 171a on the proximal end side is pushed by the opening edge of the insertion opening 184a and is displaced downward in the cutout space 165. Along with this displacement, the horizontal plate 172 gets over the four locking pieces 166 to be locked, and the vertical plate 171 blocks the insertion hole 161a of the accommodating main body 161 (refer to FIG. 15). As a result, even when the inner needle 14 advances, the needle tip 15 is guided to the needle tip accommodating hole 171b of the movable member 170 and re-exposure of the needle tip 15 is inhibited.

As described above, the catheter assembly 110 according to the second embodiment may also obtain the effect similar to that of the catheter assembly 10. Especially, the catheter assembly 110 may firmly connect the first assembly 116 to the catheter operating member 180 by the movable member 170 in the inserted state in which the inner needle 14 is inserted in the catheter 12 because the safety mechanism 160 includes the movable member 170. On the other hand, it is possible to easily separate the first assembly 116 from the catheter operating member 180 by the displacement of the movable member 170 in a non-inserted state of the inner needle 14 in the catheter 12.

Figure 19A:
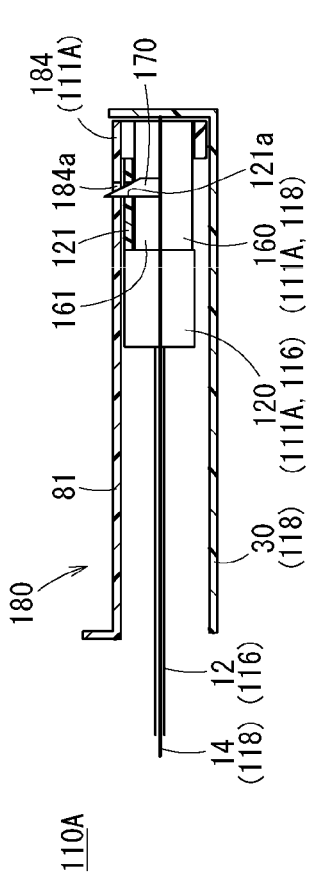
FIG. 19A is a first side sectional view schematically illustrating a catheter assembly according to a second variation.
Figure 19B:
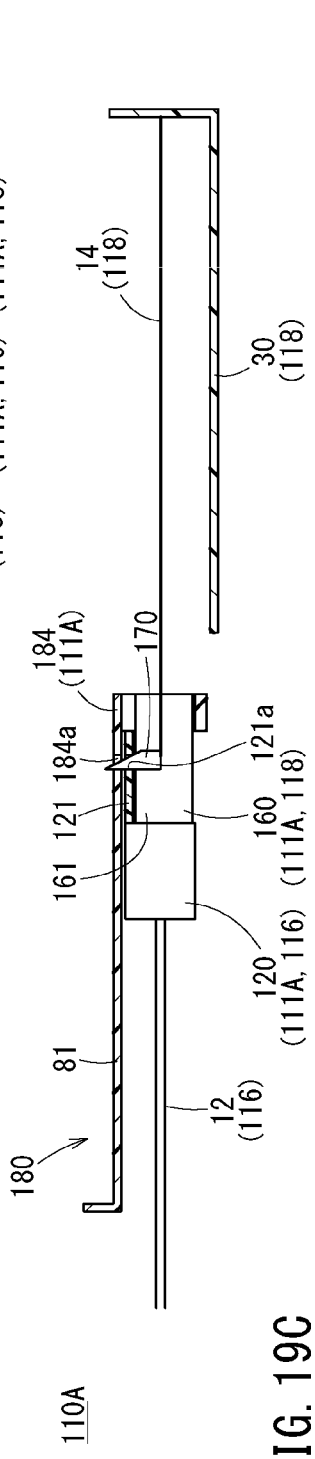
FIG. 19B is a second side sectional view of operation following FIG. 19A.
Figure 19C:
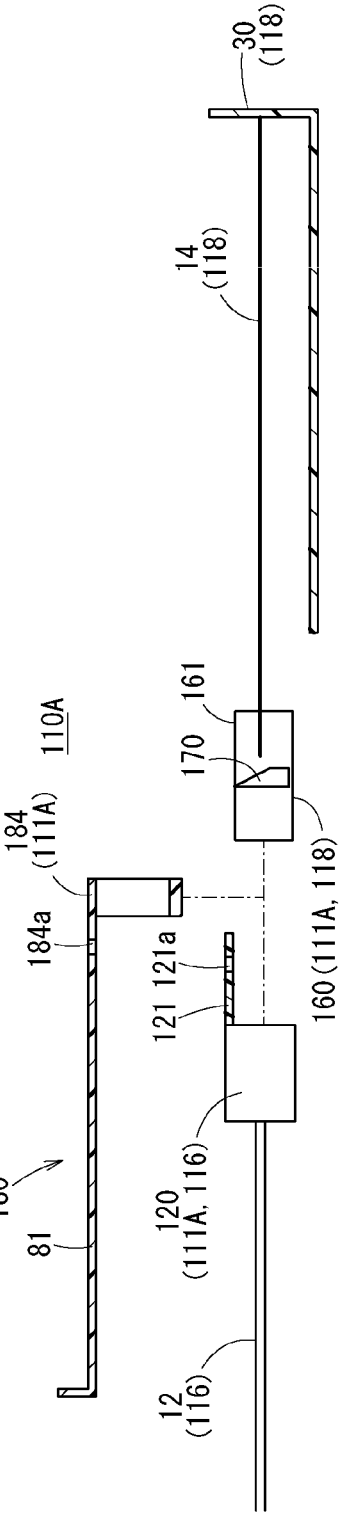
FIG. 19C is a third side sectional view of operation following FIG. 19B.
Figure 20A:
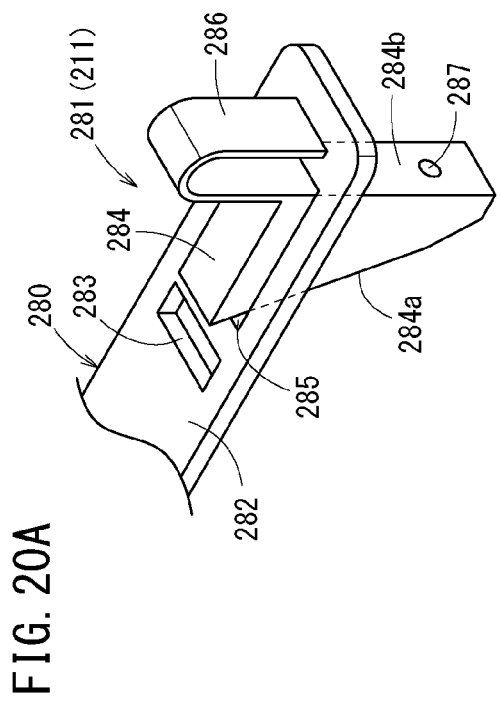
FIG. 20A is a perspective view illustrating a proximal end of a catheter operating member of a catheter assembly according to a third embodiment of the present invention.
Figure 20B:
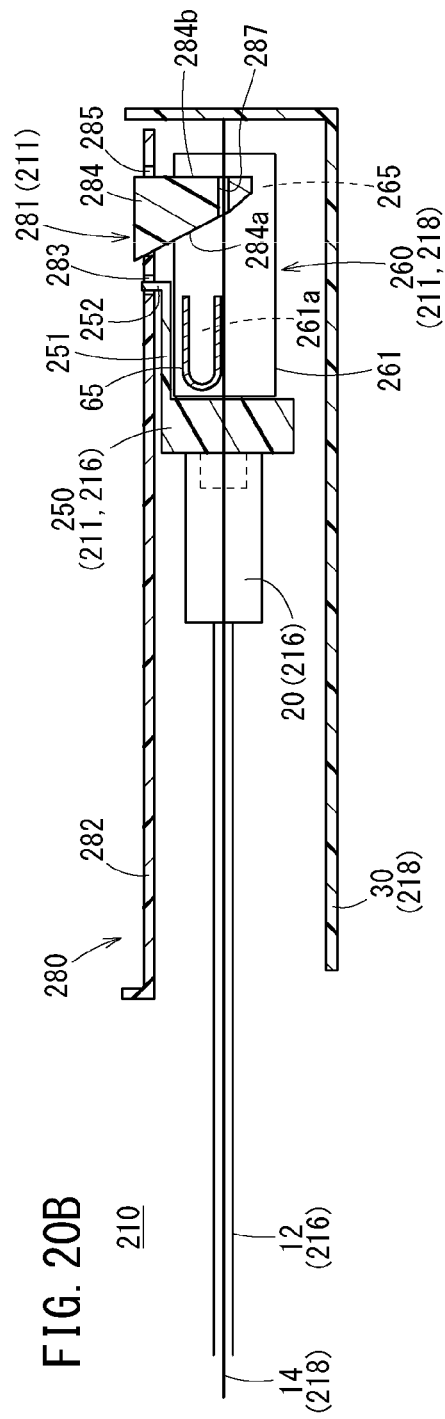
FIG. 20B is a side sectional view schematically illustrating the catheter assembly in FIG. 20A.
Figure 23A:
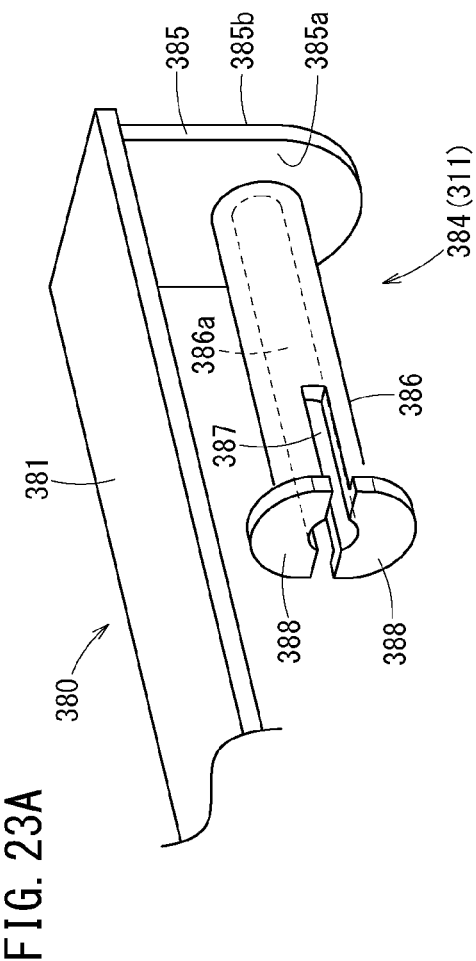
FIG. 23A is a perspective view illustrating a proximal end of a catheter operating member of a catheter assembly according to a fourth embodiment of the present invention.
Figure 23B:
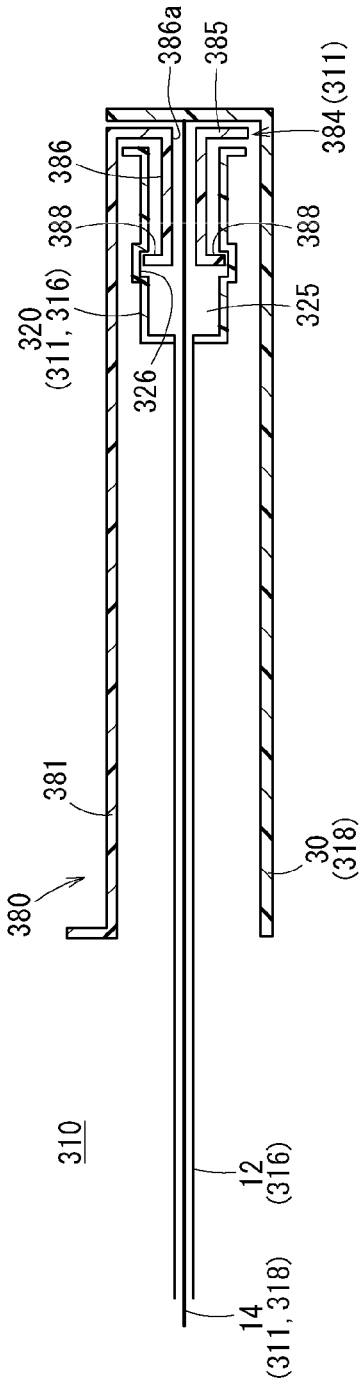
FIG. 23B is a side sectional view schematically illustrating the catheter assembly in FIG. 23A.

A catheter assembly 110A according to a second variation illustrated in FIGS. 19A to 19C has a structure of collectively performing separation restriction of a first assembly 116 and a catheter operating member 180 by a movable member 170 of a safety mechanism 160. A separation restricting mechanism 111A is formed of a catheter hub 120, the safety mechanism 160, and a connecting unit 184 of the catheter operating member 180.

Therefore, the first assembly 116 is provided with an extending portion 121 extending from a proximal end of a catheter hub 120 (or a valve mechanism 50) in a proximal end direction. The extending portion 121 is arranged between an accommodating main body 161 and the catheter operating member 180, and the movable member 170 is caught thereby. A locking hole 121a through which the movable member 170 penetrates in an initial state is provided on a proximal end side of the extending portion 121. The locking hole 121a is arranged to face an insertion opening 184a of the catheter operating member 180 in a position overlapping with the movable member 170.

The connecting unit 184 of the catheter operating member 180 is formed into a C shape in a cross-sectional view orthogonal to an axial direction, and is attached so as to enclose an outer peripheral surface of the accommodating main body 161. As a result, the catheter operating member 180 does not move any more relative to the accommodating main body 161 in a vertical direction or a width direction. In the initial state, the connecting unit 184 is provided in a position not overlapping with the extending portion 121 of the first assembly 116.

As illustrated in FIG. 19A, the catheter assembly 110A configured as described above is such that the movable member 170 is arranged in an upper position of a cutout space 165 because an inner needle 14 is inserted in the cutout space 165 in the initial state. Therefore, the movable member 170 is inserted in the locking hole 121a and the insertion opening 184a to restrict separation of the first assembly 116, the safety mechanism 160, and the catheter operating member 180.

Therefore, as illustrated in FIG. 19B, when the user performs an advancement operation of the catheter operating member 180, advancing operating force thereof is transmitted to the first assembly 116 and the safety mechanism 160 via the movable member 170, and they advance integrally. The first assembly 116 and the catheter operating member 180 are continuously locked by the movable member 170 until the needle tip 15 of the inner needle 14 moves in a proximal end direction than the movable member 170.

When the inner needle 14 exits the catheter 12 and the needle tip 15 moves in the proximal end direction than the movable member 170, the movable member 170 may be displaced to a lower portion of the cutout space 165. Therefore, as illustrated in FIG. 19C, the first assembly 116 and the catheter operating member 180 may be ejected from a distal end of the safety mechanism 160, and along with this ejection, the first assembly 116 and the catheter operating member 180 are separated.

As described above, the catheter assembly 110A according to the second variation also restricts separation of the first assembly 116, a second assembly 118, and the catheter operating member 180 in an inserted state in which an inner needle 14 is inserted in a catheter 12. Therefore, the catheter operating member 180 may smoothly operate the first assembly 116. On the other hand, when a needle tip 15 moves toward the proximal end than the movable member 170 in the non-inserted state in which the inner needle 14 exits the catheter 12, the first assembly 116, the second assembly 118, and the catheter operating member 180 are allowed to be separated and connecting strength to each other becomes weak. Therefore, the first assembly 116 is indwelled on a patient side in a satisfactory condition.

Third Embodiment

As illustrated in FIGS. 20A to 21C, a catheter assembly 210 according to a third embodiment is different from catheter assemblies 10, 10A, 110, and 110A in a structure of a catheter operating member 280 and a structure of a safety mechanism 260 (auxiliary member) corresponding to the same. A separation restricting mechanism 211 is formed of a valve mechanism 250 of a first assembly 216, the safety mechanism 260 of a second assembly 218, and a cam unit 281 (connecting unit) of the catheter operating member 280.

The catheter operating member 280 is formed as a plate-shaped plate body 282 elongated in an axial direction, and includes the cam unit 281 on a proximal end side of the plate body 282. The catheter operating member 280 also includes a catch hole 283 for catching the first assembly 216 on a side closer to a distal end than the cam unit 281.

The cam unit 281 includes a cam main body 284 (movable member) engaged with an inner needle 14, a cam hole 285 through which the cam main body 284 penetrates so as to be displaceable, a coupler 286 for coupling the plate body 282 and the cam main body 284 (not illustrated in FIGS. 20B to 21C). The cam main body 284 is formed into a trapezoidal shape in a side sectional view, and a distal end face 284a thereof is inclined toward the proximal end from an upper end toward a lower end. On a lower end side of the cam main body 284, there is provided an engagement hole 287 in which the inner needle 14 is inserted so as to penetrate from the distal end face 284a to a proximal end face 284b. The cam hole 285 is formed into a rectangular shape somewhat larger than the cam main body 284 in a plan view and the cam main body 284 is arranged inside. The coupler 286 has sufficient flexibility and allows the cam main body 284 to be displaced up and down relative to the plate body 282.

As is the case with the second embodiment, the safety mechanism 260 is formed to have a cylindrical accommodating main body 261 and includes a cutout space 265 cut out inward from an outer peripheral surface in which the cam main body 284 is inserted and includes a cavity 261a that may accommodate a shutter 65 as is the case with the first embodiment. Although not illustrated, a retaining member 68 is accommodated on a proximal end side of the cavity 261a. The cutout space 265 is communicated with an insertion hole 61a of the accommodating main body 261 in which the cam main body 284 is arranged such that the engagement hole 287 of the cam main body 284 faces the insertion hole 61a in an initial state.

In contrast, an extending portion 251 of the first assembly 216 (valve mechanism 250) has a plate shape having a predetermined length in an axial direction, and is interposed between the safety mechanism 260 and the catheter operating member 280 in the initial state. A catch projection 252 projecting upward (side opposite to the accommodating main body 261) is provided on a proximal end of the extending portion 251, and the catch projection 252 is inserted in the catch hole 283 of the catheter operating member 280.

The catheter assembly 210 according to the third embodiment is basically configured as described above, and a function effect thereof is hereinafter described. The separation restricting mechanism 211 of the catheter assembly 210 restricts separation of the valve mechanism 250, the safety mechanism 260, and the cam unit 281 of the catheter operating member 280 in an inserted state in which the inner needle 14 is inserted in a catheter 12. In this state, as in the first and second embodiments, a puncture operation and a catheter advancement operation are performed.

As illustrated in FIG. 21A, in the catheter advancement operation, a user pushes out the catheter operating member 280 in a distal end direction relative to a housing 30, so that the cam main body 284 transmits advancing operating force to the safety mechanism 260 to advance the safety mechanism 260. In addition, the catheter operating member 280 pushes out the catch projection 252 inserted in the catch hole 283 to advance the first assembly 216 together with the safety mechanism 260.

Next, the user performs an inner needle retraction operation to retract the housing 30. In the inner needle retraction operation, a needle tip 15 is accommodated in the accommodating main body 261 of the safety mechanism 260 as the inner needle 14 retracts. When the needle tip 15 moves in a proximal end direction than the shutter 65, the shutter 65 develops to face the insertion hole 61a. This inhibits re-exposure of the inner needle 14.

Furthermore, as illustrated in FIG. 21B, when the needle tip 15 further moves toward the proximal end than the cam main body 284, the needle tip 15 exits the engagement hole 287, so that the cam main body 284 may be displaced up and down. Note that the inner needle 14 is inhibited from getting out in the proximal end direction by the retaining member 68 in the safety mechanism 260. As a result, the catheter operating member 280 and the safety mechanism 260 may be separated from each other.

Therefore, when the user performs the advancement operation of the catheter operating member 280, the cam main body 284 is displaced upward with the inclined distal end face 284a abutting a wall on a distal end side of the accommodating main body 261 (cutout space 265). That is, as illustrated in FIG. 21C, the catheter operating member 280 of which separation restriction is released separates from the safety mechanism 260. While the extending portion 251 is interposed between the safety mechanism 260 and the catheter operating member 280, the first assembly 216 follows the operation of the catheter operating member 280, but this is separated from both members as the catheter operating member 280 is separated from the safety mechanism 260.

As described above, the catheter assembly 210 according to the third embodiment may also restrict the separation of the first assembly 216, the second assembly 218, and the catheter operating member 280 by the cam unit 281 in the inserted state in which the inner needle 14 is inserted in the catheter 12. On the other hand, when the needle tip 15 moves in the proximal end direction than the cam main body 284 in a non-inserted state in which the inner needle 14 separates the catheter 12, the first assembly 216, the second assembly 218, and the catheter operating member 280 are allowed to separate.

Also, a catheter assembly 210A according to a third variation has a structure of collectively restrict separation of a first assembly 216 and a second assembly 218 (safety mechanism 260A) by a cam unit 281 of a catheter operating member 280 as illustrated in FIGS. 22A to 22C. The separation restricting mechanism 211A is formed of a valve mechanism 250A, the safety mechanism 260A, and the cam unit 281 of the catheter operating member 280.

In this case, the first assembly 216 (valve mechanism 250A) is provided with an extending portion 253 including a locking hole 253a as in the second variation and is configured to catch a cam main body 284 by the locking hole 253a. Accordingly, it is possible that the catheter assembly 210A is not provided with a catch projection 252 and a catch hole 283 of the catheter operating member 280.

In an initial state, the catheter assembly 210A inserts the cam main body 284 in the locking hole 253a of the first assembly 216 and a cutout space 265 of the safety mechanism 260A, and restricts the separation of the first assembly 216, the safety mechanism 260A, and the catheter operating member 280. When a needle tip 15 of an inner needle 14 moves toward a proximal end than the cam main body 284 at the time of an inner needle retraction operation, the cam main body 284 becomes displaceable. As a result, the cam main body 284 may get out of the cutout space 265 and the locking hole 253a, and the separation of the first assembly 216, the safety mechanism 260A, and the catheter operating member 280 is allowed.

As described above, the catheter assembly 210A according to the third variation may also obtain an effect similar to that of the catheter assembly 210 according to the third embodiment. Especially, the catheter assembly 210A is connected to both the first and second assemblies 216 and 218 by the cam main body 284 of the catheter operating member 280 in the inserted state (separation is restricted), so that a configuration may be made simple.

Fourth Embodiment

As illustrated in FIGS. 23A to 24C, a catheter assembly 310 according to a fourth embodiment is different from catheter assemblies 10, 10A, 110, 110A, 210, and 210A in a structure that a catheter operating member 380 engages in a catheter hub 320 in an initial state. A separation restricting mechanism 311 is formed of the catheter hub 320 of a first assembly 316, an inner needle 14 of a second assembly 318, and a connecting unit 384 of the catheter operating member 380.

The connecting unit 384 of the catheter operating member 380 is inserted in a hollow portion 325 of the catheter hub 320 and switchingly engaged with and disengaged from the catheter hub 320 on the basis of an inserted state and a non-inserted state of the inner needle 14 of the second assembly 318. The connecting unit 384 includes a hanging plate 385 projecting downward from a lower surface on a proximal end side of a plate body 381 of the catheter operating member 380 and a connecting tube 386 projecting from the hanging plate 385 by a predetermined length.

The hanging plate 385 is firmly coupled to the lower surface of the plate body 381 of the catheter operating member 380 to arrange the connecting tube 386 at a predetermined height. The connecting tube 386 is firmly coupled to a distal end face 385a of the hanging plate 385, and an insertion hole 386a in which the inner needle 14 is inserted is provided therein. The insertion hole 386a penetrates to a proximal end face 385b of the hanging plate 385.

A pair (a plurality) of slits 387 communicated with the insertion hole 386a and vertically dividing the connecting tube 386, and a locking flange 388 projecting radially outward from a body portion to be locked by the catheter hub 320 are provided on a distal end side of the connecting tube 386. The distal end side of the connecting tube 386 divided by a pair of slits 387 may be shaped in a direction such that the divided portions come close to each other. As a result, when the engagement is released, the connecting tube 386 and the catheter hub 320 are easily separated. Note that the divided portions may extend in parallel to each other. In contrast, the catheter hub 320 is provided with a locking groove 326 that circulates in a circumferential direction on an inner surface forming the hollow portion 325.

In the catheter operating member 380, the inner needle 14 is inserted also in the insertion hole 386a of the connecting tube 386 in the inserted state in which the inner needle 14 is inserted in the catheter 12. In this state, the divided portions on the distal end side of the connecting tube 386 are pushed by an outer peripheral surface of the inner needle 14 to be separated from each other, and the locking flange 388 at the distal end is caught by the locking groove 326. As a result, the connecting tube 386 is inhibited from getting out of the catheter hub 320, and movement of the catheter operating member 380 in a vertical direction or a width direction with respect to the first assembly 316 and the second assembly 318 including the inner needle 14 is restricted.

Therefore, as illustrated in FIG. 24A, when the user advances the catheter operating member 380, advancing operating force is transmitted to the first assembly 316 via the locking portion of the locking flange 388 and the locking groove 326, and the hanging plate 385 and a proximal end of the catheter hub 320. As a result, the first assembly 316 and the catheter operating member 380 may be advanced relative to the inner needle 14.

As illustrated in FIG. 24B, when the inner needle 14 moves toward the proximal end than the connecting tube 386 of the catheter operating member 380, the divided portions of the connecting tube 386 come close to each other and locking of the locking flange 388 and the locking groove 326 is released. That is, as illustrated in FIG. 24C, the separation of the first assembly 316 from the catheter operating member 380 is allowed on the basis of a fact that the inner needle 14 exits the catheter operating member 380 in the non-inserted state in which the inner needle 14 separates from the catheter 12. As a result, the first assembly 316 may be indwelled in a satisfactory condition on a patient side.

As described above, the catheter assembly 310 according to the fourth embodiment may also obtain the effect similar to that of the catheter assemblies 10, 10A, 110, 110A, 210, and 210A. Especially, the catheter assembly 310 is such that the connecting unit 384 is directly connected to the inner needle 14 so as to be slidable in the catheter hub 320, so that the engagement between the second assembly 318 and the catheter operating member 380 becomes simple. Note that the catheter assembly 310 is not limited to the above-described configuration, and for example, the first assembly 316 may be provided with the valve mechanism 50.

As in a catheter assembly 310A according to a fourth variation illustrated in FIGS. 25A to 25C, a safety mechanism 360A (auxiliary member) for accommodating a needle tip 15 of an inner needle 14 may also be added to the configuration of the catheter assembly 310 described above. That is, a separation restricting mechanism 311A is formed of a catheter hub 320A of a first assembly 316, a safety mechanism 360A of a second assembly 318, and a connecting unit 384 of a catheter operating member 380.

For example, the safety mechanism 360A of the catheter assembly 310A is formed into a tubular shape accommodated in an insertion hole 386a of the connecting unit 384 (connecting tube 386) of the catheter operating member 380. Divided portions of the connecting tube 386 are pushed from inside by the safety mechanism 360A in an inserted state in which the inner needle 14 is inserted in the catheter 12, so that a locking flange 388 is caught by a locking groove 326. Therefore, separation of the catheter hub 320A, the safety mechanism 360A, and the connecting unit 384 is restricted.

When the housing 30 and the inner needle 14 are moved in a proximal end direction, the vicinity of the needle tip 15 is caught by the safety mechanism 360A (for example, a retaining member 68), and the safety mechanism 360A is retracted. As a result, the safety mechanism 360A separates from the connecting tube 386, and in the separated state, re-exposure of the inner needle 14 is inhibited by an appropriate mechanism (for example, a shutter 65). In a non-inserted state, separation of the first assembly 316, the second assembly 318, and the catheter operating member 380 may be allowed as locking of the locking flange 388 and the locking groove 326 is released.

Fifth Embodiment

A catheter assembly 410 according to a fifth embodiment is configured such that a catheter operating member 480 is directly engaged with an inner needle 14 of a second assembly 418 so as to be slidable on a side closer to a proximal end than a catheter hub 20 as illustrated in FIGS. 26 to 28C. A separation restricting mechanism 411 is formed of the catheter hub 20 of a first assembly 416, the inner needle 14 of the second assembly 418, and a connecting unit 484 of the catheter operating member 480.

Figure 26:
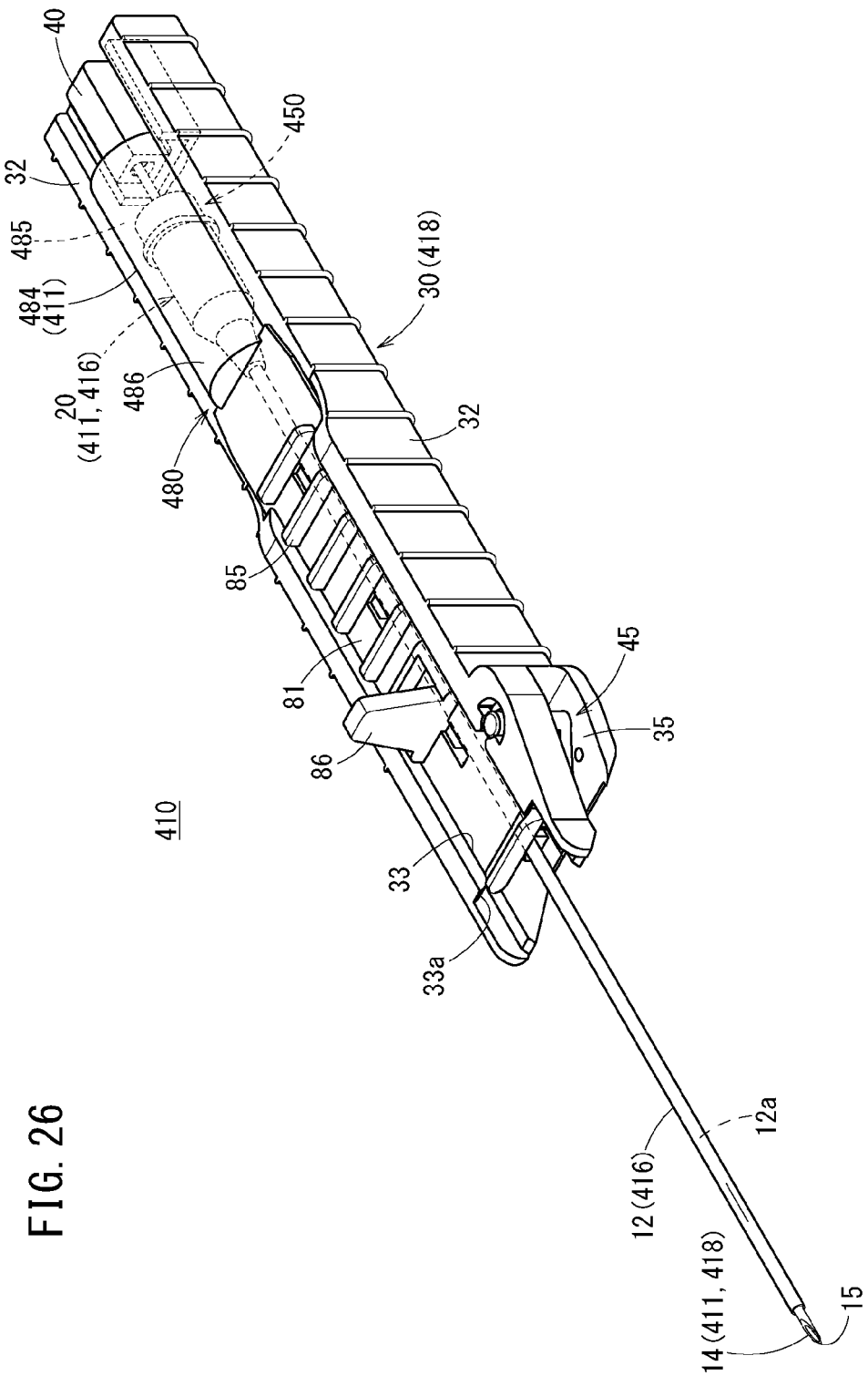
FIG. 26 is a perspective view illustrating an entire configuration of a catheter assembly according to a fifth embodiment.
Figure 27:
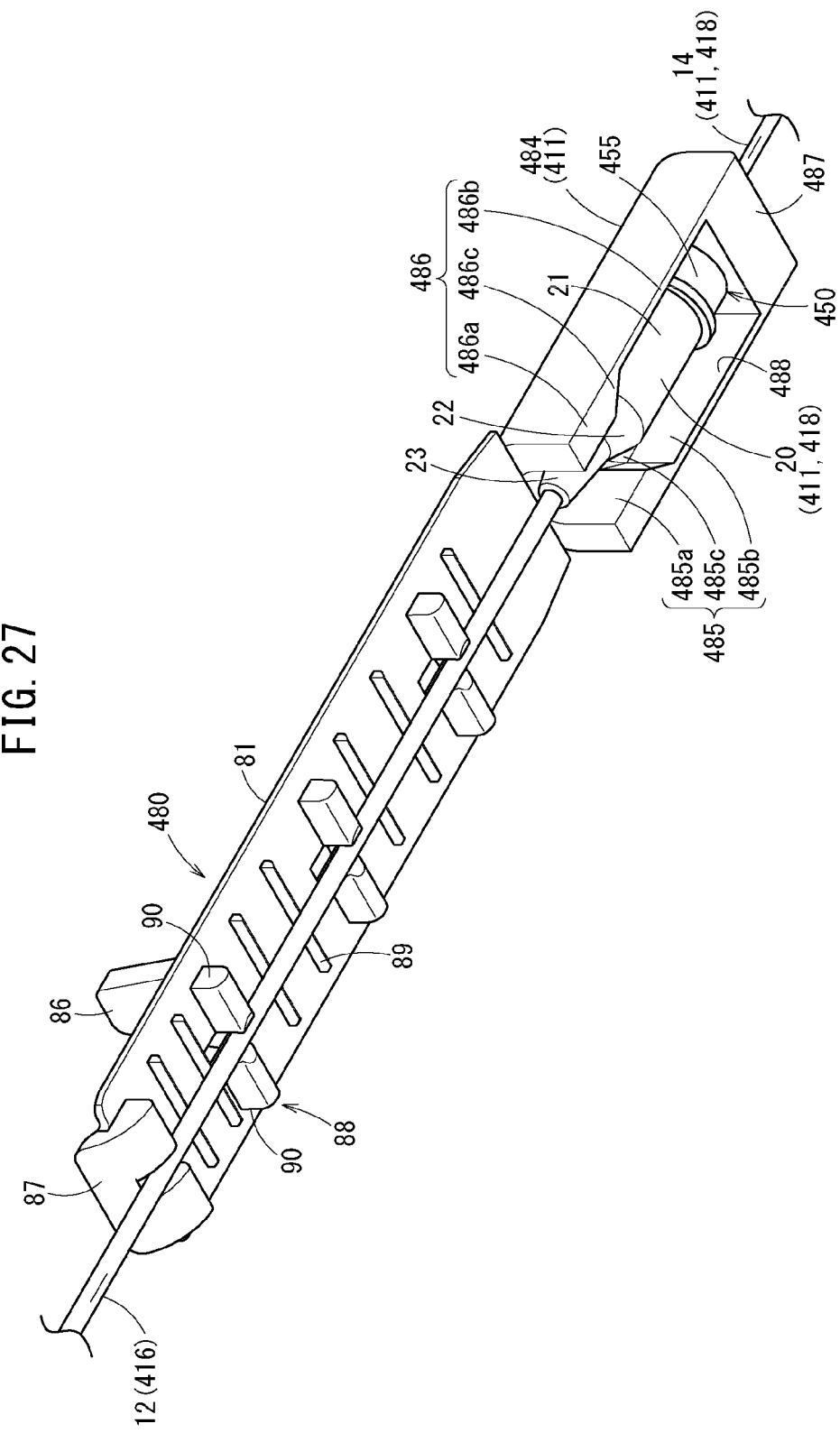
FIG. 27 is a perspective view illustrating a state in which a catheter hub is accommodated in a catheter operating member in FIG. 26.
Figure 28A:
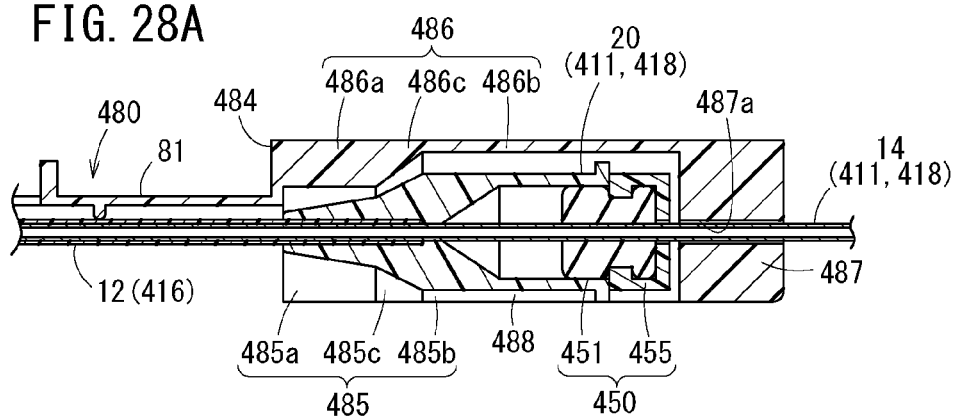
FIG. 28A is a first side sectional view illustrating a substantial part of the catheter operating member and the catheter hub in FIG. 27.

As illustrated in FIGS. 26, 27 and 28A, the catheter operating member 480 is provided with the connecting unit 484 coupled to a proximal end of an operating plate 81 and accommodates the catheter hub 20 in an accommodating chamber 485 in the connecting unit 484 in an initial state. In a cross-sectional view orthogonal to an axial center of the connecting unit 484, the connecting unit 484 is provided with an arch-like tubular wall 486 formed of an arc-shaped upper wall and side walls linearly extending downward from both ends in a circumferential direction of the upper wall (that is, having a semi-tubular shape as a whole). A lower side of the tubular wall 486 is formed in a flat shape parallel to an axial direction of the connecting unit 484 and is provided with an opening portion 488 communicated with the accommodating chamber 485.

A length in the axial direction of the connecting unit 484 is somewhat longer than a length in the axial direction of the catheter hub 20 to which the valve mechanism 450 is attached. Both the catheter hub 20 and the valve mechanism 450 are accommodated in the accommodating chamber 485. Note that this catheter assembly 410 is not provided with a safety mechanism. Therefore, although the valve mechanism 450 is formed of a valve main body 451 and a connector 455 (having no structure to catch the safety mechanism) having substantially the same functions as those of the valve main body 51 and the connector 55 of the first embodiment, the length in the axial direction thereof is slightly shorter than that of the other embodiments. Note that the valve mechanism 450 may also be formed only of the valve main body 451 (elastic member).

While an outer peripheral surface side of the tubular wall 486 of the connecting unit 484 is continuous with a constant outer diameter (dimension), an inner peripheral surface side thereof changes according to an outer shape of the catheter hub 20. Specifically, a distal end side wall portion 486a bulges radially inward so that a distal end side accommodating chamber 485a is a small space, and a proximal end side wall portion 486b is formed to be thinner than the distal end side wall portion 486a so that a proximal end side accommodating chamber 485b is a large space. In this case, a lateral width of the distal end side accommodating chamber 485a is formed to be smaller than a diameter of a large-diameter portion 21 of the catheter hub 20. Between the distal end side wall portion 486a and the proximal end side wall portion 486b, an intermediate side wall portion 486c that increases the space in a tapered manner toward the proximal end direction is formed to form an intermediate side accommodating chamber 485c.

In the initial state, the distal end side accommodating chamber 485a accommodates a small-diameter portion 23 of the catheter hub 20, the intermediate side accommodating chamber 485c accommodates a transition portion 22 of the catheter hub 20, and the proximal end side accommodating chamber 485b accommodates the large-diameter portion 21 of the catheter hub 20. The inner peripheral surfaces of the distal end side wall portion 486a, the proximal end side wall portion 486b, and the intermediate side wall portion 486c are designed to have dimensions separated to a certain degree radially outward from the outer peripheral surface of the catheter hub 20 so as to accommodate the catheter hub 20 in a non-contact manner within the accommodating chamber 485.

In addition, while the connecting unit 484 opens a distal end of the accommodating chamber 485, this closes a proximal end side of the accommodating chamber 485 by a blocking wall 487 (wall portion) continuous to the semi-tubular proximal end side wall portion 486b. An inner needle through hole 487a through which the inner needle 14 may penetrate is provided in a predetermined position of the blocking wall 487. That is, in the initial state, the blocking wall 487 is directly connected to the inner needle 14. In the initial state, the blocking wall 487 is arranged on a distal end side of a needle holding member 40 and comes into contact with a proximal end of the valve mechanism 450 by advancing operating force of a user to push out the first assembly 416.

Also, because the intermediate side wall portion 486c is formed into a tapered shape, this faces a distal end side of the transition portion 22 of the catheter hub 20. Therefore, the intermediate side wall portion 486c comes into contact with the transition portion 22 of the catheter hub 20 and retracts the first assembly 416 with a retraction operating force by the user transmitted.

The catheter assembly 410 described above is such that the inner needle 14 is also inserted in the connecting unit 484 of the catheter operating member 480 in an inserted state in which the inner needle 14 is inserted in the catheter 12, thereby restricting separation of the catheter hub 20, the inner needle 14, and the connecting unit 484 of the catheter operating member 480. That is, the catheter hub 20 is restricted from moving in a direction other than the axial direction of the inner needle 14 by the inner needle 14 inserted therein, and because this is in the accommodating chamber 485, relative movement (movement in the axial direction and in a separating direction) with respect to the catheter operating member 480 is restricted.

When the user performs an advancement operation of the catheter operating member 480 in a distal end direction, the blocking wall 487 pushes the valve mechanism 450 to relatively advance the first assembly 416 with respect to the inner needle 14. On the other hand, when the user performs a retraction operation of the catheter operating member 480 in the proximal end direction, the intermediate side wall portion 486c pushes the catheter hub 20 in the proximal end direction to relatively retract the first assembly 416 with respect to the inner needle 14. Also, when the catheter operating member 480 advances, the tubular wall 486 comes into contact with a supporting member 45, so that the supporting member 45 may be satisfactory rotated.

Figure 28B:
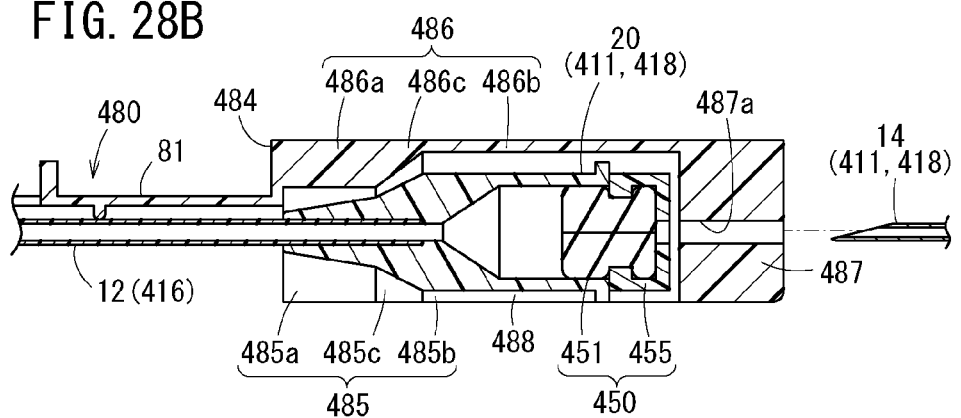
FIG. 28B is a second side sectional view of operation following FIG. 28A.
Figure 28C:
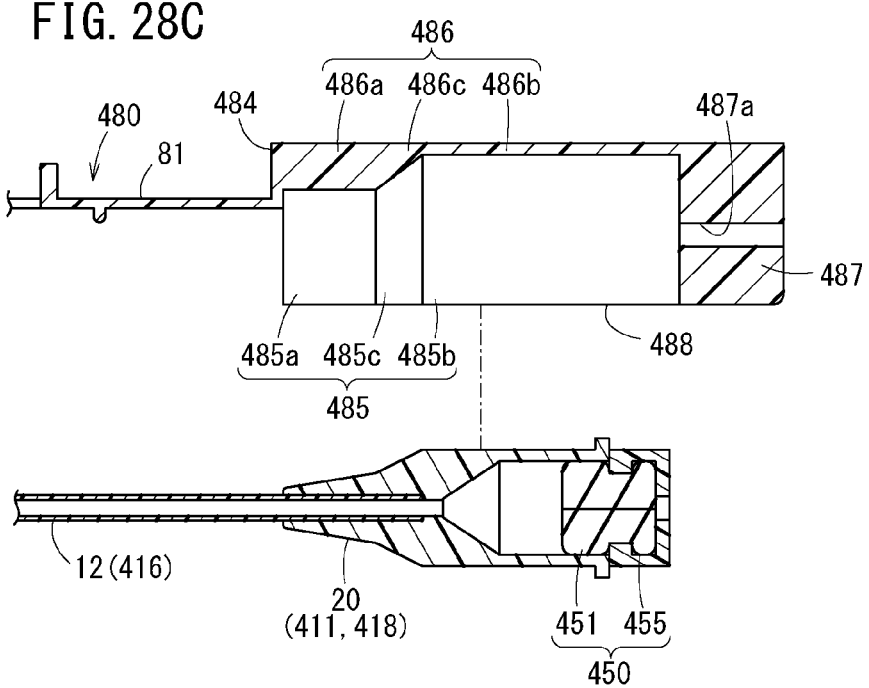
FIG. 28C is a third side sectional view of operation following FIG. 28B.

Then, as illustrated in FIG. 28B, when the inner needle 14 exits the connecting unit 484 in the proximal end direction (that is, in a non-inserted state), the catheter operating member 480 is in a free state with respect to the inner needle 14. Separation of the catheter hub 20 originally accommodated in a non-contact manner with the catheter operating member 480 is also allowed. Therefore, as illustrated in FIG. 28C, the first assembly 416 is such that the catheter hub 20 easily exits the opening portion 488 of the connecting unit 484 downward. After the catheter hub 20 separates from the catheter operating member 480, an operator removes the valve mechanism 450 from the catheter hub 20. As a result, the catheter 12 and the catheter hub 20 are indwelled in a satisfactory condition on a patient side.

As described above, the catheter assembly 410 (separation restricting mechanism 411) according to the fifth embodiment may also obtain the effect similar to that of the catheter assemblies 10, 10A, 110, 110A, 210, 210A, 310, and 310A. Especially, the catheter assembly 410 has a simple configuration in which the inner needle 14 is slidably connected to the connecting unit 484 in a proximal end position of the catheter hub 20. Therefore, reduction in manufacturing cost and the like are further promoted.

In addition, because the connecting unit 484 covers an upper portion and a side portion of the catheter hub 20, it is possible to inhibit the catheter hub 20 and the housing 30 from coming into contact with each other when the catheter operating member 480 moves, thereby suppressing the catheter hub 20 from shaking. Furthermore, the connecting unit 484 may reduce a chance that the user touches and contaminates the catheter hub 20. Also, because an inner peripheral surface of the connecting unit 484 is separated from the outer peripheral surface of the catheter hub 20 and connecting strength is zero, when the inner needle 14 is separated, the catheter hub 20 may be separated from the catheter operating member 480 without force. Furthermore, the catheter assembly 410 is such that the inner needle 14 is inserted in the valve main body 451 and the connector 455, thereby inhibiting the inner needle 14 and the first assembly 416 from shaking.

Note that it is a matter of course that the catheter assembly 410 may also adopt various configurations. For example, although the inner peripheral surface of the connecting unit 484 is separated radially from the outer peripheral surface of the catheter hub 20 in the above-described embodiment, it is also possible to configure such that the inner peripheral surface of the connecting unit 484 comes into contact with the catheter hub 20 to apply some frictional force.

Also, for example, the valve mechanism 450 (valve main body 451) may be provided inside the catheter hub 20. Furthermore, on a side surface of the catheter hub 20, an extension tube (including a side hole in which the extension tube may be attached) or a port to which an infusion set may be connected may be provided. Furthermore, the catheter assembly 410 may have a safety mechanism as described in the other embodiments. For example, the safety mechanism may engage with the first assembly 416 (refer also to a fifth variation described later) or the catheter operating member 480 in the initial state and engage with the needle tip 15 to separate as the inner needle 14 retracts.

Figure 29A:
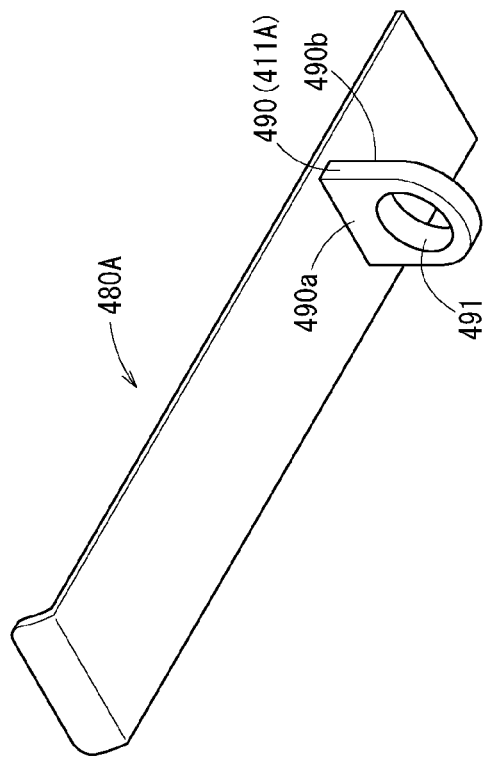
FIG. 29A is a perspective view illustrating a catheter operating member of a catheter assembly according to a fifth variation.
Figure 29B:
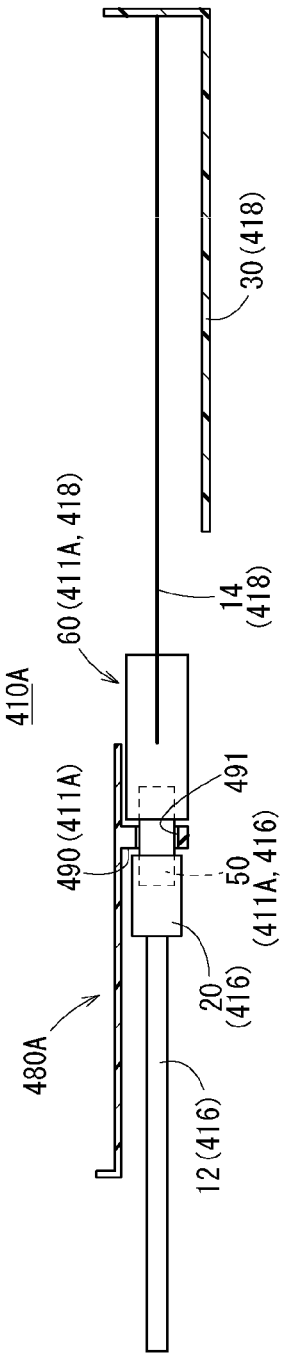
FIG. 29B is a side sectional view schematically illustrating the catheter assembly in FIG. 29A.

A catheter assembly 410A according to a fifth variation illustrated in FIGS. 29A and 29B is configured to surround an entire circumference of a valve mechanism 50 by a ring-shaped connecting unit 490 of a catheter operating member 480A. Also, the catheter assembly 410A is provided with the valve mechanism 50 and a safety mechanism 60 as in the first embodiment. A separation restricting mechanism 411A is formed of the valve mechanism 50 of a first assembly 416, the safety mechanism 60 of a second assembly 418, and the connecting unit 490 of the catheter operating member 480A.

The connecting unit 490 of the catheter operating member 480A has a certain thickness in a longitudinal direction of the catheter operating member 480A. The connecting unit 490 is provided with an arranging hole 491 penetrating a distal end face 490a and a proximal end face 490b; the arranging hole 491 in which the valve mechanism 50 is arranged is formed so as to be smaller than an outer annular convex portion 58 of the valve mechanism 50 and an outer tube 71 in diameter (refer also to FIG. 3). Because the arranging hole 491 penetrates through the valve mechanism 50 between the catheter hub 20 and the safety mechanism 60, relative displacement of the connecting unit 490 in vertical and width directions with respect to the first and second assemblies 416 and 418 is restricted.

When the catheter operating member 480A advances, the connecting unit 490 comes into contact with the valve mechanism 50 to transmit advancing operating force to the first assembly 416 and the safety mechanism 60. When retracting, the connecting unit 490 comes into contact with the outer tube 71, and transmits a retraction operating force to the first assembly 416 and the safety mechanism 60. After an inner needle 14 is removed from a catheter 12 and the valve mechanism 50 and the safety mechanism 60 are separated from each other, the connecting unit 490 is removed from a proximal end of the valve mechanism 50, and the first assembly 416 and the catheter operating member 480A are easily separated.

As described above, the catheter assembly 410A according to the fifth variation may also obtain the effect similar to that of the catheter assemblies 10, 10A, 110, 110A, 210, 210A, 310, 310A, and 410. Especially, the catheter assembly 410A has a simple structure in which the connecting unit 490 does not cover a side portion of the catheter hub 20, and work efficiency and the like at the time of manufacturing are further improved.

In a catheter assembly 410B according to a sixth variation illustrated in FIGS. 30A to 30C, as in the catheter assembly 410A according to the fifth variation, a connecting unit 492 of a catheter operating member 480B is formed into a ring shape projecting to a lower surface of the plate body 481. The connecting unit 492 includes an engagement hole 493 penetrating through a distal end face 492a and a proximal end face 492b in which an inner needle 14 is slidably inserted and is directly connected so as to be slidable with respect to the inner needle 14 in an initial state. Also, in the initial state, the connecting unit 492 is arranged so as to be contactable with a proximal end of a catheter hub 20 of a first assembly 416, thereby transmitting advancing operating force of the catheter operating member 480B to the catheter hub 20 of the first assembly 416.

The catheter operating member 480B is provided with an operating projection 494 in a position away from the connecting unit 492 in a distal direction by a predetermined interval (for example, a length in an axial length of the catheter hub 20). The operating projection 494 interposes the catheter hub 20 in an axial direction in cooperation with the distal end face 492a of the connecting unit 492 and transmits a retraction operating force of the catheter operating member 480B. The operating projection 494 may interpose a flange 24 between the same and the connecting unit 492.

Therefore, in an inserted state in which the inner needle 14 is inserted in the catheter 12, the inner needle 14 is also inserted in the connecting unit 492 of the catheter operating member 480B, restricting separation of the catheter hub 20, the inner needle 14, and the connecting unit 492 of the catheter operating member 480B. When the catheter operating member 480B advances relative to the inner needle 14 and the inner needle 14 exits the engagement hole 493 of the connecting unit 492 (that is, in a non-inserted state), the separation of the catheter hub 20, the inner needle 14, and the catheter operating member 480B is allowed.

As described above, the catheter assembly 410B (separation restricting mechanism 411B) according to the sixth variation may also obtain the effect similar to that of the catheter assemblies 10, 10A, 110, 110A, 210, 210A, 310, 310A, 410, and 410A. Note that the catheter assembly 410B may also adopt various configurations and, for example, the first assembly 416 may include a valve mechanism 450.

The present invention is not limited to the above-described embodiments, and it goes without saying that various modifications may be made without departing from the spirit of the present invention.

What is claimed is:

1. A catheter assembly comprising:
   a first assembly comprising:
      a catheter, and
      a catheter hub that fixes and holds the catheter;
   a second assembly comprising:
      an inner needle removably inserted in the catheter and the catheter hub, and
      a needle hub that fixes and holds the inner needle; and
   a catheter operating member that controls relative movement of the first assembly with respect to the second assembly in an axial direction of the inner needle, the catheter operating member comprising:
      a connecting unit on a proximal side of the catheter hub, the connecting unit including a distal-most end face, a proximal-most end face, and an engagement hole penetrating from the distal-most end face to the proximal-most end face, wherein the inner needle is slidably inserted in the engagement hole and in direct contact with the connecting unit, and
      an operating projection positioned away from the connecting unit at a predetermined interval in the axial direction of the inner needle,
   wherein, when the inner needle is in an inserted state in which the inner needle is inserted in the catheter hub and the engagement hole, a portion of a proximal-most end face of the operating projection contacts a portion of a distal-most end face of the catheter hub and a portion of the distal-most end face of the connecting unit contacts a portion of a proximal-most end face of the catheter hub,
   wherein, when the inner needle is in a non-inserted state in which the inner needle is separated from the catheter hub and positioned entirely outside of the engagement hole, a distal end of the inner needle is exposed, and
   wherein (i) when the inner needle is in the inserted state, the connecting unit allows movement of the first assembly in the axial direction but restricts separation of the first assembly from the catheter operating member, and (ii) when the inner needle is in the non-inserted state, the connecting unit allows separation of the first assembly from the catheter operating member.

2. The catheter assembly according to claim 1, wherein the predetermined interval is a length in an axial direction of the catheter hub.

3. The catheter assembly according to claim 1, wherein the catheter operating member further comprises a plate body and the connecting unit projects from a lower surface of the plate body.

4. The catheter assembly according to claim 3, wherein: the operating projection extends from the lower surface of the plate body.

5. The catheter assembly according to claim 4, wherein the connecting unit is ring shaped.

6. A method of using a catheter assembly, the method comprising:
   providing a catheter assembly comprising:
      a first assembly comprising:
         a catheter, and
         a catheter hub that fixes and holds the catheter;
      a second assembly comprising:
         an inner needle removably inserted in the catheter and the catheter hub, and
         a needle hub that fixes and holds the inner needle; and
      a catheter operating member that controls relative movement of the first assembly with respect to the second assembly in an axial direction of the inner needle, the catheter operating member comprising:
         a connecting unit on a proximal side of the catheter hub, the connecting unit including a distal-most end face, a proximal-most end face, and an engagement hole penetrating from the distal-most end face to the proximal-most end face, wherein the inner needle is slidably inserted in the engagement hole and in direct contact with the connecting unit, and
         an operating projection positioned away from the connecting unit at a predetermined interval in the axial direction of the inner needle,
      wherein, when the inner needle is in an inserted state in which the inner needle is inserted in the catheter hub and the engagement hole, a portion of a proximal-most end face of the operating projection contacts a portion of a distal-most end face of the catheter hub and a portion of the distal-most end face of the connecting unit contacts a portion of a proximal-most end face of the catheter hub,
      wherein, when the inner needle is in a non-inserted state in which the inner needle is separated from the catheter hub and positioned entirely outside of the engagement hole, a distal end of the inner needle is exposed,
   placing the inner needle in the inserted state in which the connecting unit allows movement of the first assembly in the axial direction but restricts separation of the first assembly from the catheter operating member; and
   placing the inner needle in the non-inserted state in which the connecting unit allows separation of the first assembly from the catheter operating member.

* * * * *